US009775632B2

(12) United States Patent
Pansky et al.

(10) Patent No.: US 9,775,632 B2
(45) Date of Patent: Oct. 3, 2017

(54) METHOD AND DEVICE FOR RECANALIZATION OF TOTAL OCCLUSIONS

(75) Inventors: Amir Pansky, Atlit (IL); Oleg Weizman, HerzliYa (IL); Alexander Melamud, Nesher (IL)

(73) Assignee: Medinol Ltd., Tel Aviv (IL)

( * ) Notice: Subject to any disclaimer, the term of this patent is extended or adjusted under 35 U.S.C. 154(b) by 1090 days.

(21) Appl. No.: 12/470,745

(22) Filed: May 22, 2009

(65) Prior Publication Data
US 2009/0292296 A1 Nov. 26, 2009

Related U.S. Application Data

(63) Continuation-in-part of application No. 12/325,868, filed on Dec. 1, 2008, now abandoned.

(60) Provisional application No. 61/055,942, filed on May 23, 2008.

(51) Int. Cl.
A61B 17/22 (2006.01)
A61B 17/00 (2006.01)
A61B 90/00 (2016.01)

(52) U.S. Cl.
CPC .. A61B 17/22012 (2013.01); *A61B 17/22022* (2013.01); *A61B 2017/00141* (2013.01); *A61B 2017/00154* (2013.01); *A61B 2017/00199* (2013.01); *A61B 2017/00539* (2013.01); *A61B 2017/22001* (2013.01); *A61B 2017/22015* (2013.01); *A61B 2017/22038* (2013.01); *A61B 2017/22049* (2013.01); *A61B 2017/22094* (2013.01); *A61B 2090/064* (2016.02)

(58) Field of Classification Search
CPC .... A61B 17/22012; A61B 2017/00154; A61B 2017/00539; A61B 2017/22094

USPC .................................................. 606/127, 159
See application file for complete search history.

(56) References Cited

U.S. PATENT DOCUMENTS

| 3,785,382 | A | 1/1974 | Schmidt-Kloiber et al. |
| 4,419,598 | A | 12/1983 | Spitz et al. |
| 4,920,954 | A | 5/1990 | Alliger et al. |

(Continued)

FOREIGN PATENT DOCUMENTS

| DE | 3812841 | 11/1989 |
| EP | 0 554 616 | 8/1993 |

(Continued)

OTHER PUBLICATIONS

PCT International Search Report and Written Opinion from corresponding PCT Application No. PCT/IB2009/052159 dated Dec. 16, 2009.

(Continued)

*Primary Examiner* — Julie A Szpira
(74) *Attorney, Agent, or Firm* — Cadwalader, Wickersham & Taft LLP

(57) ABSTRACT

An apparatus, system and method for re-canalization or opening a passage through an occlusion in a blood vessel is disclosed. The apparatus and method, which are appropriate for both cardiovascular as well as peripheral vessels, use hydraulic pressure to drive a vibratable member, and the system includes a control unit to permit the frequency or amplitude of oscillation of the vibratable member to be adjusted to suit the morphology or hardness of the target occlusion. Also disclosed is a method for adjusting the force of vibration.

49 Claims, 10 Drawing Sheets

(56) References Cited

U.S. PATENT DOCUMENTS

| | | | |
|---|---|---|---|
| 5,380,273 | A | 1/1995 | Dubrul et al. |
| 5,425,735 | A | 6/1995 | Rosen et al. |
| 5,549,119 | A | 8/1996 | Solar |
| 5,836,940 | A * | 11/1998 | Gregory .................. 606/15 |
| 5,928,186 | A * | 7/1999 | Homsma et al. ............ 604/22 |
| 5,941,869 | A | 8/1999 | Patterson et al. |
| 5,964,223 | A | 10/1999 | Baran |
| 6,237,606 | B1 * | 5/2001 | Zikorus et al. ............ 128/898 |
| 6,348,040 | B1 | 2/2002 | Stalker et al. |
| 6,441,716 | B1 | 8/2002 | Doppalapudi et al. |
| 6,652,536 | B2 * | 11/2003 | Mathews et al. ........... 606/113 |
| 6,688,162 | B2 | 2/2004 | Bachas et al. |
| 7,062,981 | B1 | 6/2006 | Spohr |
| 7,137,963 | B2 | 11/2006 | Nita et al. |
| 7,220,233 | B2 * | 5/2007 | Nita et al. .................. 601/2 |
| 7,297,131 | B2 | 11/2007 | Nita |
| 2003/0181785 | A1 * | 9/2003 | Viebach et al. ............ 600/152 |
| 2004/0193182 | A1 * | 9/2004 | Yaguchi et al. ............ 606/128 |
| 2005/0119679 | A1 | 6/2005 | Rabiner et al. |
| 2007/0021690 | A1 | 1/2007 | Nita et al. |

FOREIGN PATENT DOCUMENTS

| | | |
|---|---|---|
| EP | 0 788 774 | 8/1997 |
| WO | WO 91/10403 | 7/1991 |
| WO | WO 93/06780 | 4/1993 |
| WO | WO 2005/106417 | 11/2005 |
| WO | WO 2007/095191 | 8/2007 |
| WO | WO 2007/132464 | 11/2007 |

OTHER PUBLICATIONS

Cardiovascular Research Foundation (CVRF), "PCI for Chronic Total Occlusion: Guiding Catheter and Guidewire," CTO Live, Japan Asan Medical Center held Jan. 6, 2007.

Gorski, Kenneth A., "Chronic Total Occlusions: New Devices to Treat Peripheral Vascular Disease," Sones Cardiac Catherization Laboratories, The Cleveland Clinic Foundation, http://www.europeronline.com/fo/lecture/view_slide.php?id=2847, accessed on Feb. 15, 2008.

Kensey Nash, Endovascular Innovation, "Safe-Cross, RF CTO System" Brochure, http://www.macropore.com/pdf/3621SafeCrossBrochure.pdf, accessed on Feb. 15, 2008.

Sintef Electronics and Cybernetics, "Piezoresistive Pressure Sensors", http://www.fys.uio.no/~livfur/FYS4230/piezoelecture.pdf, accessed on Mar. 18, 2008.

Stone, et al., "Percutaneous Recanalization of Chronically Occluded Coronary Arteries: A Consensus Document: Part II," American Heart Association, http://circ.ahajournals.org/cgi/content/full/112/16/2530, 2005.

* cited by examiner

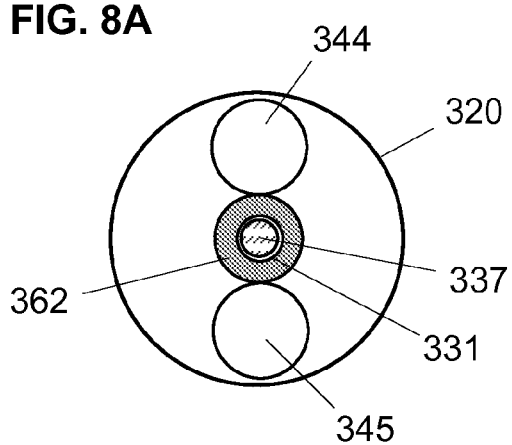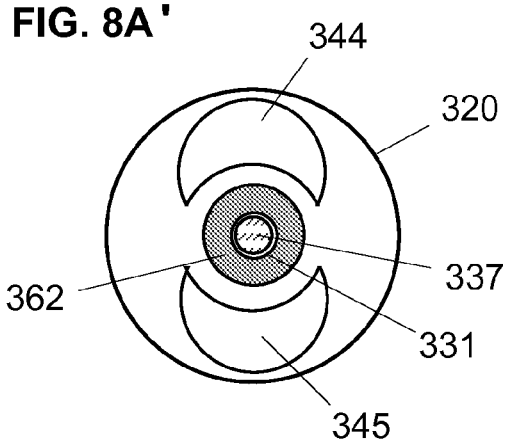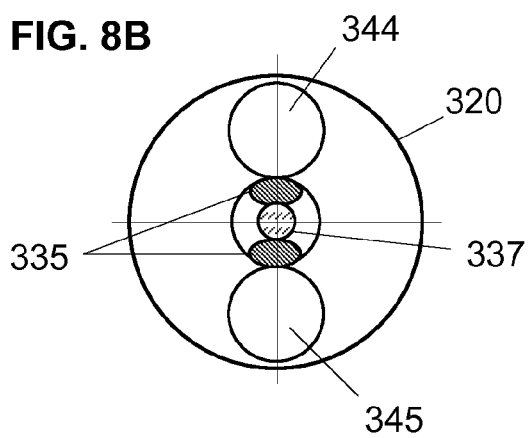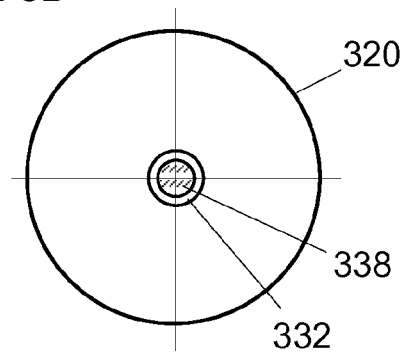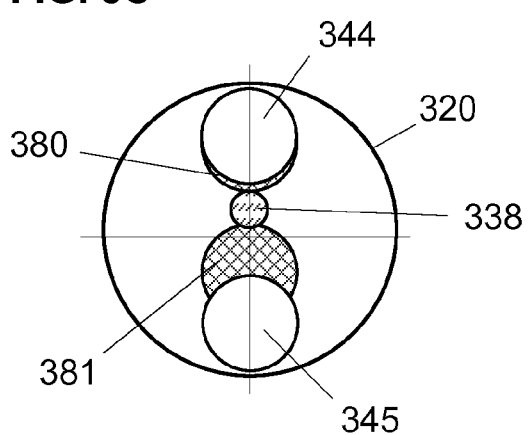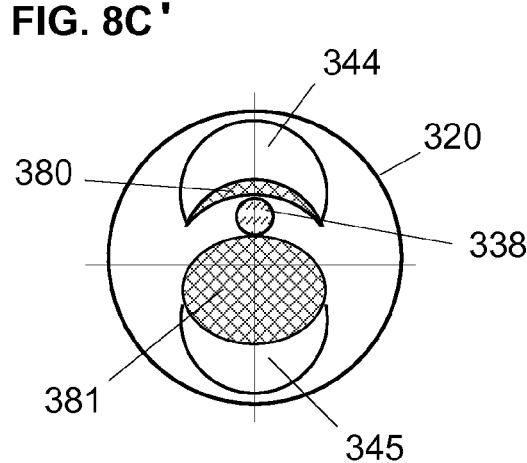

METHOD AND DEVICE FOR RECANALIZATION OF TOTAL OCCLUSIONS

FIELD OF THE INVENTION

The invention is directed to an energy delivery system and method of using that system for penetrating a total occlusion of a blood vessel during percutaneous coronary intervention ("PCI"). In particular, the system provides adjustable transmission of energy to match occlusion morphology and adequate energy transfer to the distal tip of the PCI device to penetrate the occlusion. The system is also applicable to percutaneous intervention procedures in peripheral arteries.

BACKGROUND OF THE INVENTION

Medical science has long sought effective treatments for disease conditions involving stenosis (narrowing or obstruction) of the lumen of an artery. This condition, known generally as an occlusion, occurs in patients suffering from atherosclerosis, which is characterized by an accumulation of fibrous, fatty or calcified tissue in the arteries, otherwise known as atheromata or plaques. An occlusion may be partial or total; it may be soft and pliable or hard and calcified. Occlusions can arise at a great variety of sites in the arterial system including the aorta, the coronary and carotid arteries, and peripheral arteries. An occlusion can result in hypertension, ischemia, angina, myocardial infarction, stroke and even death.

Minimally invasive procedures are the preferred treatment of arterial occlusions. In these procedures, a catheter—a long, highly flexible tubular device—is introduced into a major artery through a small arterial puncture made in the groin, upper arm or neck. The catheter is advanced and steered into the site of the stenosis. A great variety of devices have been developed for operating upon the stenosed artery, and these devices are placed at the distal end of the catheter and delivered thereby. Example procedures include percutaneous transluminal coronary angioplasty (PTCA), directional coronary atherectomy (DCA), and stenting.

In a total occlusion, a passageway must first be opened through the occlusion to allow the balloon/stent catheter to be placed in the target stenosed segment of the vessel. As occlusion morphology is complicated and varies from patient to patient, common methods and devices for opening these occlusions have limited success and require long procedures with potentially adverse effects on the patient. Such adverse effects include perforation of blood vessel wall, high radiation dose or damage to kidneys due to extensive use of angiographic contrast material.

Stenoses, or occlusions, are made of a variety of materials—from softer fatty substances such as cholesterol, to tougher fibrous material, to hard calcified material. Generally the ends of the occlusion—the proximal and distal caps—comprise the harder calcified material. The harder materials are more difficult to penetrate, requiring a significant amount of energy, the softer materials require less energy. Therefore, opening an occlusion requires transfer of relatively extensive energy to the distal end of a catheter or guide wire, especially when calcification is present. Additionally, the form of energy required to penetrate such an occlusion may differ from occlusion to occlusion, which differences generally are only realized during the procedure.

Some available methods for opening total occlusions are radio-frequency ablative energy (as used in system sold by Intralumenal Therapeutics as Safecross™), vibrational energy of about 20 kHz and small amplitudes (as used in system sold by FlowCardia Inc. as Crosser™), dedicated stiff guide wire which pushes a passage through the occlusion (as developed by Asahi Intec Co. and distributed as Confianza 9g/Conquest and Miracle 12g guide wires) and mechanical vibration elements working at high frequency (Crosser™). The latter suffer from significant energy loss between the energy source at the proximal end of the catheter and the driller located at the distal end of the catheter, as well as limited working life due to material fatigue. For example, with an ultrasound catheter, the ultrasonic energy usually originates from an ultrasound transducer at the proximal end of the catheter and is then transmitted to the distal head of the catheter as a sinusoidal wave, causing the distal head to vibrate and either ablate or disrupt the target occlusion. To reach treatment sites, such catheters must be rather long—about 150 cm or more—and therefore a large amount of energy must initially be transmitted to reach the distal end. At the same time, to be flexible enough to course through highly tortuous vessels, the wires must be reasonably thin. The long length and narrow diameter combine to make wire breakage a common problem due to the stress and wear from the high energy pulses. Guide wires stiff enough to penetrate hard occlusions have the disadvantage that their inflexibility and straight tips make navigating through tortuous vessels difficult and increase the risk of vessel perforation. All such devices provide limited success rate ranging from 40-70%.

Occlusions comprise a variety of materials of different density and hardness. Therefore, the nature of the energy used in a re-canalization device should suit the specific occlusion and the penetration should be controlled to prevent perforation of the artery walls or damage to healthy tissue. Additionally, because the energy originates at the proximal end of the catheter it must be able to reach the distal end of the device near the occlusion at a level sufficient to effect penetration of the occlusion without damaging the conductive wires and without sacrificing flexibility of the device. As previously described, current devices suffer either from an insufficient amount of energy transferred to the distal end of the device or a mismatch between the type of energy delivered and the type of occlusion, sometimes resulting in too much force being applied and thereby increasing the risk of damage, or even perforation, of the lumen wall. Accordingly, there is a need for a system or apparatus that can transfer adequate energy to the re-canalization device, and there is a need for a system that can adjust the amount of energy transmitted to the penetrating end of the device based on the hardness of the occlusion.

Additionally, because the total occlusion prevents blood flow to the vessel downstream of the occlusion, conventional X-ray fluoroscopy imaging is incapable of imaging both the occluded section of the vessel and the downstream portion of the vessel. Thus, there is also a need for an improved re-canalization system that is compatible with techniques permitting visualization of the re-canalization device and surrounding tissue during the PCI procedure.

SUMMARY OF THE INVENTION

It is an object of the invention to provide an improved apparatus for penetrating a vessel occlusion, where the apparatus has a vibratable member that is made to vibrate in an improved manner.

The invention is directed to an apparatus and system for re-canalization of a total occlusion in a body lumen, such as a blood vessel. In particular, the apparatus of the invention comprises a hydraulic catheter and a vibrational energy source operably connected to the hydraulic catheter. The hydraulic catheter comprises at least one hydraulic lumen. The vibrational energy source is adapted to input energy pulses, preferably hydraulic pressure waves or pulses, into the at least one hydraulic lumen of the hydraulic catheter. The hydraulic lumen and hydraulic catheter may be the same structure, or the hydraulic catheter may be a conventional interventional medical device such as a catheter but also contains at least one hydraulic lumen. The hydraulic lumen is capable of efficiently transferring energy to a vibratable member at its distal tip to oscillate that vibratable member to penetrate an occlusion in a body lumen. The system of the invention comprises a hydraulic catheter, a vibrational energy source operably connected to the hydraulic catheter and a control unit adapted to control the vibrational energy source, i.e., to adjust the energy input into the hydraulic catheter. Preferably, the energy input may be adjusted to generate a vibration force suitable for the occlusion morphology and hardness, the vibration force having at least one frequency and at least one amplitude. Suitable vibration force may be achieved by adjusting the frequency, e.g., from several Hz to several hundred Hz, and/or adjusting the amplitude, so that the penetration force of the vibration is minimized and is appropriate for the occlusion morphology and hardness. The hydraulic catheter is compatible for use with additional external or internal components that assist visualization of the apparatus or device and/or assist with guiding the apparatus or device through the vessel and occlusion. The invention is further directed to a method of using the apparatus or system for recanalization of an occluded body lumen, such as a blood vessel, and a method of controlling the force of vibration in the apparatus. The result is a versatile energy delivery apparatus, system and method for penetrating a total occlusion.

Specifically, the apparatus of the invention comprises a hydraulic catheter, having a proximal end and a distal end, and a vibrational energy source. The hydraulic catheter has at least one hydraulic lumen and a catheter head at its distal end. The hydraulic lumen is a sealed structure containing a liquid, preferably a biologically compatible liquid, and having a proximal end and a distal end. The hydraulic lumen preferably comprises a proximal element, a distal element and a hydraulic tube connecting the proximal element to the distal element. The hydraulic lumen itself may be the hydraulic catheter or it may be a lumen within the hydraulic catheter. The vibrational energy source is external of the catheter, but is operably connected thereto, in particular to the hydraulic lumen of the hydraulic catheter. Preferably, the vibrational energy source is a hydraulic energy source that is capable of generating at least one of hydraulic pressure wave, comprising at least one frequency and at least one amplitude, into the hydraulic lumen preferably via the proximal element of the hydraulic lumen. The proximal element may mediate initiating the hydraulic pressure wave through the hydraulic tube preferably by being mechanically compressed or shaken in the proximal direction. The hydraulic tube transmits the hydraulic pressure wave to the distal element. The distal element may be a vibratable member or may effect oscillation of a vibratable member, which vibration is driven by the hydraulic pressure wave. The catheter head, which is the distal-most region of the hydraulic catheter, comprises the distal element.

Within the catheter head, the distal element of the hydraulic lumen cooperates with the hydraulic pressure waves to generate a vibration force useful for penetrating a vessel occlusion. The catheter head comprises three functional components: a vibratable member, a return force component and an occlusion impact element. The vibratable member oscillates in response to the distally directed force from the hydraulic pressure waves and the proximally-directed force of the return force component. The vibration motion of the vibratable member is transferred to the occlusion impact element, which effects penetration of the occlusion. These three functional components may comprise one or more structures. For example: the distal element of the hydraulic lumen may be a structure that performs all three functions; the distal element of the hydraulic lumen may transmit a vibration energy and return force to a separate structure that is a vibratable member and occlusion impact element; or a structure (or combination of structures) separate from the distal element of the hydraulic lumen may comprise all three functional components. Preferably, the three functional components are built into the distal element of the hydraulic lumen.

As noted above, the energy or force for driving the vibratable member preferably is hydraulic pressure generated from an external source—a vibrational energy source. The vibrational energy source may be a transducer, to transform, e.g., electrical power to hydraulic power, or electrical power to mechanical power and then mechanical power to hydraulic power, to generate a hydraulic wave or pulse in the hydraulic lumen. Preferably, the vibrational energy source is an actuator. An advantage of the hydraulic pressure feature of the invention is that the force will not significantly diminish in strength from the proximal end of the hydraulic catheter where the energy is transmitted to the distal end of the device where the vibratable member drills through the occlusion. Further, the vibration force may be adjusted and amplified without being significantly limited by the external power source.

The system of the invention comprises the apparatus and a control unit for controlling the vibration energy source, and thus the frequency and/or amplitude of vibration of the vibratable member. The at least one frequency and at least one amplitude generated by the vibrational energy source may be adjusted via the control unit to suit the occlusion being treated. Optionally, the system of the invention further comprises an operator interface unit and a tissue sensor to assist the operator in controlling the frequency and amplitude of the hydraulic pressure waves based on feedback from the tissue sensor regarding hardness of the occlusion.

It is believed that by providing the minimal force necessary to penetrate an occlusion, safety of the recanalization procedure is increased and potential damage to the body lumen, e.g., an artery, is reduced compared to recanalization devices in the art. Accordingly, the frequency and/or amplitude of vibration of the vibratable member may be changed manually by the physician operator to adjust for the hardness of the particular occlusion being treated, based on the operator's skill and experience. Alternatively, the frequency and amplitude of vibration may be adjusted automatically or manually based on measurements of the hardness of the occlusion. Where the hardness of the occlusion is to be measured, the apparatus of the invention may further comprise a tissue sensor or strain gauge. In such embodiments, the control unit may further comprise a processor, or an operator interface unit comprising a processor may be used, the processor being capable of analyzing input from the tissue sensor or strain gauge to calculate tissue hardness and the operator interface unit being capable of providing the calculations in a user-readable form. Either the control unit or operator interface unit may comprise one or more adjustor means for the operator to adjust manually the frequency and/or amplitude of the hydraulic energy generated by the vibrational energy source. Optionally, the operator interface unit may further comprise a display unit for displaying information regarding occlusion hardness.

The apparatus may additionally comprise a device that secures the catheter relative to the blood vessel to improve the delivery vibration forces to the occlusion. The apparatus may still further comprise a catheter head steering device to assist navigation through an occlusion, especially for use in cases where there are numerous bifurcations near the target occlusion.

DESCRIPTION OF DRAWINGS

FIG. 1 shows a schematic diagram depicting an embodiment of the system of the invention.

FIG. 2 shows schematic diagrams of a hydraulic catheter embodiment according to the invention.

FIG. 3 shows schematic diagrams of a hydraulic catheter embodiment according to the invention.

FIG. 4 depicts schematic diagrams detailing hydraulic catheters according to various embodiments of the invention.

FIG. 5 depicts schematic diagrams of catheter head embodiments of an apparatus according to the invention including a hydraulic lumen comprising a distal bellows as a vibratable member. In particular.

FIG. 6 depicts schematic diagrams of catheter head embodiments of an apparatus according to the invention comprising an elastic membrane as a vibratable member.

FIG. 7 depicts schematic diagrams of the catheter head of a dual lumen hydraulic system comprising the distal end of a guide wire as a vibratable member and drilling pin.

FIG. 8 depicts cross-sections through the catheter head of FIG. 7B at different positions, proximal to distal, in FIG. 7B indicated as 8A, 8B, 8C, and 8D, to further illustrate the details of that embodiment. FIGS. 8A and 8A' depict the cross-sectional shapes of two embodiments of the dual hydraulic lumen, and illustrate the dual hydraulic lumen embodiments at a proximal position of the catheter head—position 8A of FIG. 7B—to show the relative positions of the components. FIG. 8B depicts a cross-section through the dual hydraulic lumen embodiment at position 8B of the catheter head of FIG. 7B and illustrates the relative positions of the components. FIG. 8C and FIG. 8C' depict cross-sectional shapes of two embodiments of the dual hydraulic lumen, and illustrate the dual hydraulic lumen embodiments of the catheter head at position 8C of FIG. 7B, where one of the expandable membrane of a hydraulic lumen has flexed the guide wire, to show the relative positions of the components. FIG. 8D illustrates a cross-section through the dual hydraulic lumen embodiment at position 8D of the catheter head of FIG. 7B, where distal end of the guide wire exits the catheter through a guide wire short lumen.

FIG. 9 is a series of schematic diagrams depicting components of a tissue sensor according to the invention.

DETAILED DESCRIPTION OF THE INVENTION

Figure 1A:
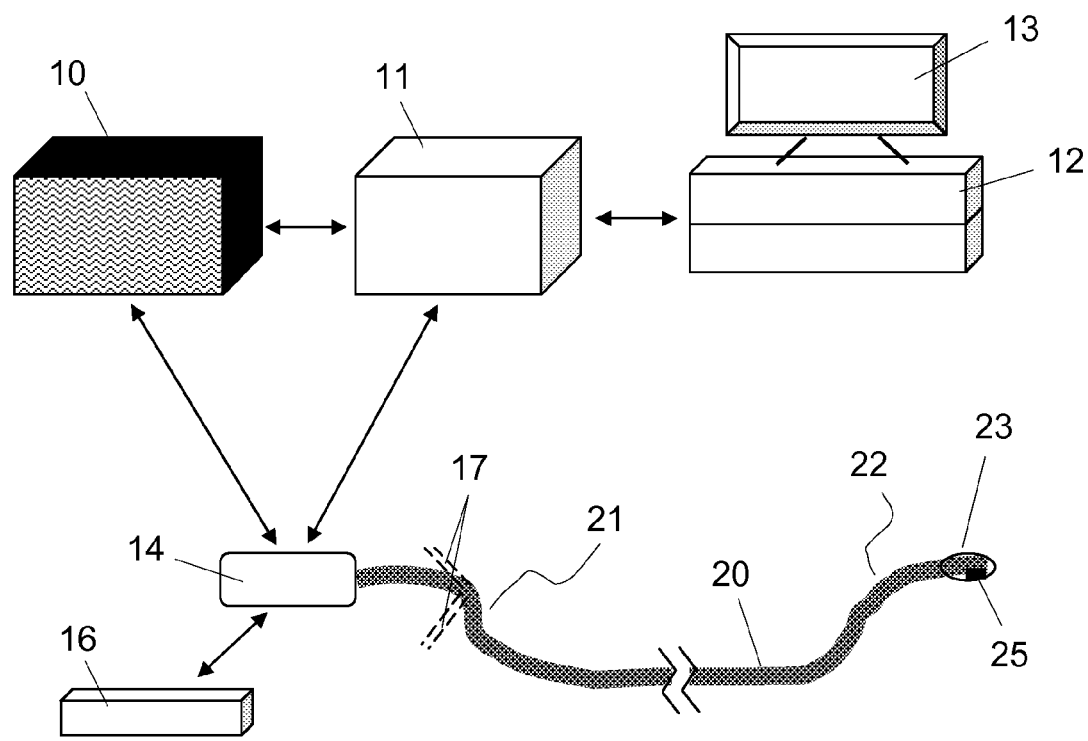
FIG. 1A shows a vibrational energy source, a control unit and a hydraulic catheter apparatus comprising a tissue sensor.

The apparatus, system and method of the invention provide an improved device and method for re-canalization of a total occlusion in a blood vessel. The device of the invention may also be applicable to clearing occlusions of other body lumens. Specifically, the apparatus of the invention is a hydraulic catheter comprising a hydraulic lumen—a sealed hydraulic system that preferably comprises a proximal element, a distal element and a hydraulic tube or pipe sealingly connecting the proximal element to the distal element—and a vibrational energy source operably connected thereto. The apparatus of the invention provides therapeutic vibration in a vibratable member located in the catheter head at the distal end of the hydraulic catheter, for example, an intravenous hydraulic catheter. The force for generating therapeutic vibration of the vibratable member is provided by the vibrational energy source, which is capable of generating at least one hydraulic pressure wave or pulse. The hydraulic lumen contains a liquid, preferably a biocompatible liquid, wherein vibrational energy input may be received by the proximal element and propagated as a hydraulic pressure wave via the hydraulic tube to the distal element. The distal element may function as a vibratable member or may transfer the vibration energy to a vibratable member, for penetrating an occlusion in a body lumen. Preferably, the frequency and amplitude of the hydraulic pressure waves or pulses generated by the vibrational energy source are controllable via a control unit. The system of the invention provides an apparatus, as described above, operably connected to a control unit, for controlling the frequency and/or amplitude of vibration of the hydraulic pressure waves (and thus indirectly also the frequency and/or amplitude of vibration of the vibrating member). The invention provides a method of treating an occlusion wherein the apparatus, and preferably the system, of the invention is used to recanalize an occlusion. Also provided is a method of controlling the force of vibration.

The vibrational energy source may be a vibrational shaker—for example, an actuator, hydraulic solenoid or standard motor—with an element of compressing liquid. The vibrational energy source is external of the hydraulic catheter and generates hydraulic pressure pulses into the hydraulic lumen, preferably via the proximal element. The hydraulic energy is transmitted through the hydraulic lumen distally, preferably via the hydraulic tube to the distal element, to oscillate a vibratable member at a frequency and amplitude to sufficiently penetrate and clear a vessel occlusion.

In particular, the hydraulic catheter of the invention is defined by having a hydraulic lumen, which is a closed system containing a liquid and capable of transmitting at least one hydraulic pressure wave or pulse from a proximal end to a distal end. For example, the liquid within the hydraulic lumen may be made to move via an external force as one or more pressure waves within three parts of the lumen—a proximal element, a distal element and a hydraulic pipe or tube that sealingly connects the proximal and distal elements. The proximal and distal elements, but not the hydraulic tube, may be made to expand and contract. The preferred method of causing expansion of the distal element is to reduce the volume of the proximal member, as the total volume of the closed system does not change. The distal element may be made to vibrate or oscillate by pushing liquid into it, thereby expanding it, and then removing the pressure, thereby allowing it to "spring back". Active expansion of the proximal element or other return mechanisms also may be used to assist as a return force component for the distal element. The vibrational energy source may initiate a plurality of hydraulic pressure waves by repeated compression (and optionally expansion) of the proximal element. In use, vibration is limited to relevant components in the catheter head.

Hydraulic systems permit longitudinal displacement amplification by pushing liquid from large volumes to small volumes. As the displaced volume is very small (e.g., $0.4 \times 0.4 \times 0.1$ mm$^3$), the vibrational energy source may move a small amount of liquid with very small displacement. Optionally, the hydraulic lumen includes proximal and/or distal active bellows that can serve to amplify the hydraulic energy transmitted through the hydraulic catheter. Hydraulic amplification, or gain, is set by having area ratio of the distal and proximal parts according to $V=A \cdot L$, where V is the displaced volume, A is the cross sectional area of the tube at the proximal or distal end, and L is the displacement distance. The volume of the hydraulic lumen is constant. Therefore, as pressure is exerted on the proximal bellows by the mechanical plunger to compress $L_p$—the length of the proximal bellows, the volume of the distal bellows must increase (extending the distal bellows) thereby increasing $L_d$—the length of the distal bellows. Where the cross-sectional area of the proximal bellows is larger than the cross-sectional area of the distal bellows, longitudinal displacement amplification may occur, as $L_d$ will be larger than $L_p$.

Other advantages of the hydraulic system of the invention are that little energy is lost (as illustrated by the above equation), minimal heat is generated, and simple and low cost catheters may be employed. It is further contemplated that the apparatus of the invention may comprise any one of several means to achieve one or more of the goals, and that more than one combination of these means may be used, embodiments of which are described below. Further, the system of the invention comprises the apparatus, a vibrational energy source and a control unit for controlling the frequency or amplitude of the vibrational energy. The system is designed to control the force exerted on the occlusion, by permitting the frequency and amplitude of vibration to be changed or adjusted, so as to provide a penetration force proportional to the hardness of the occlusion. The invention also comprises a method of using the apparatus to treat a vessel occlusion, and a method of controlling the frequency or amplitude of vibration of the vibratable member.

A vibrational force, causing vibration of a vibratable member at a frequency sufficient for the occlusion impact element to penetrate an occlusion, is provided by a hydraulic pressure pulse or wave in combination with a return force. The hydraulic pressure pulse drives the vibratable member forward (distally), the return mechanism returns the vibratable member proximally to its resting position. The vibratable member within the catheter head is directly exposed to the hydraulic lumen. Preferably, the vibratable member is part of the hydraulic lumen, e.g., the distal element. Alternatively, the hydraulic lumen has components to cause the vibratable member to oscillate.

Without being restricted to a specific mechanism, the components of the invention operate in general terms as follows. The vibratable member is made to vibrate by combined action of the hydraulic pressure waves and return force component. Penetration and traversal of the occlusion is achieved through cooperation of three functional elements of the catheter head—the vibratable member, return force component, and occlusion impact element—in conjunction with energy from the hydraulic pressure waves. The occlusion impact element is the therapeutic component of the catheter head that physically contacts the occlusion during penetration and traversal. The specific mechanism for oscillating the vibratable member and/or penetrating the occlusion will depend on the particular embodiment, but all embodiments employ a hydraulic energy system.

As noted previously, the three functional components of the catheter head—the vibratable member, the return force component and the occlusion impact element—may be met by fewer than or more than 3 structures. With an understanding of the invention as described herein, the person having ordinary skill in the art will be able to implement the elements of the apparatus and system of the invention as set forth herein to arrive at an array of combinations that will function alone or in conjunction with known components of endovascular devices in accordance with the goals of the invention.

The vibratable member may be, for example, an active bellows, an elastic membrane, a guide wire, a vibration cap, a spring, a coated spring, or similar member suitable for vibrating within a catheter at a frequency and amplitude sufficient to penetrate a vessel occlusion via an occlusion impact element. The oscillation of the vibratable member occurs by combined action of the hydraulic pressure and return force component.

The return force may be active or passive but provides a force to or within the vibratable member in the proximal direction. Preferably, the structure that is the vibratable member has an intrinsic return force component. Optionally, more than one return force component may be used. The return energy for the vibratable member may be provided by one or more return force components, for example, the intrinsic spring of an active bellows, the elasticity of an elastic membrane or of an extensible lumen wall, the flexibility of a guide wire, one or more springs, a plurality of pulling wires, or similar mechanisms suitable for returning the hydraulic pressure waves and/or the vibratable member.

The occlusion impact element is the component that contacts the occlusion to be penetrated. The occlusion impact element, may be a region of a vibratable member structure or separate from the vibratable member structure. Preferably, the occlusion impact element is a region of the structure that is the vibratable member. An occlusion impact element may comprise the distal end of an active bellows—which may further comprise a surface having a particular contour, the outer surface of an elastic membrane, distal impact end of a guide wire, a driving surface of a vibration cap at the distal end of a catheter, or other suitable structure for penetrating an occlusion.

In one embodiment, the distal element of the hydraulic lumen is an active bellows that functions as a vibratable member, a return force component and an occlusion impact element within the catheter head. As used herein, an active bellows is essentially a sealed element which has a return force built into it, for example, a sealed coated spring or corrugated tube comprising a spring element. The active bellows may have an open design or a closed design. By "closed design" is meant that one end of the bellows is closed, as a cup; by "open design" is meant that both ends of the bellows are open, as a tube. In either case, the active bellows, as all vibratable members in accordance with the invention, is functionally attached to the hydraulic lumen. For the closed design, the closed end would be located at the distal end. The structures of these active bellows may be designed so that they may be expanded upon load pressure and returned (contracted) by the internal spring force upon removal of the external pressure; according to the invention, the distal active bellows are intended to operate in this fashion. The structures of these active bellows also may be designed so that they may be either expanded or compressed upon load pressure, and then contracted or expanded (respectively) to a resting state by the internal spring force upon removal of the external force. Active bellows useful in the present invention are available from, for example, MS Bellows, 5322 McFadden Ave, Huntington Beach, Calif. 92649. The terms "bellows" "active bellows" and "spring bellows" are used interchangeably herein. Alternatively, the ordinarily skilled artisan can make a distal bellows by covering a spring with a polymer or embedding a spring in a polymer, such that the polymer membrane is extensible in the longitudinal direction relative to the hydraulic catheter and is capable of withstanding the hydraulic pressure inside. Preferably the polymer material has a lower durometer (shore) than the material making up the outer walls of the catheter.

When used in accordance with the invention, a bellows is coextensive with the hydraulic lumen, in other words it is sealingly connected to the hydraulic lumen, forming an integral part of the hydraulic lumen, whether at the proximal end or the distal end of the hydraulic lumen. The hydraulic lumen may have a proximal bellows and a distal bellows. The distal bellows may be a vibratable member according to the invention, and may also provide the return force and occlusion impact element functions. The proximal bellows may be functionally connected to the vibration energy source, so as to receive at least one energy pulse to generate a hydraulic wave through the hydraulic lumen. A proximal bellows may be used in conjunction with a distal bellows or in conjunction with a non-bellows vibratable member at the distal end of the hydraulic lumen.

According to one embodiment of the invention, the distal bellows are active bellows intended to expand upon pressure load and contract upon removal of the pressure load. The hydraulic pressure pulse or wave causes expansion of the distal active bellows. As the distal bellows is a sealed spring, it intrinsically contains a return force, however additional return force may be provided by additional components. Preferably, additional return force is provided. The vibrational energy source may be, for example, a solenoid that moves a mechanical plunger. The plunger may be attached to the proximal bellows to cause it to contract and expand. In this arrangement, the plunger may provide a return force component for the distal bellows. Thus, a mechanical plunger may provide the hydraulic push force, whether or not it is secured to the proximal bellows, and the distal bellows may provide a return force component, alone or in combination with other structures. In either arrangement thereby, the liquid inside the hydraulic lumen can be made to move distally and proximally causing the distal bellows in turn to expand and contract. A distal cap or impact end may be placed on the distal end of the distal bellows and may have any of various contoured surfaces. Thus, active bellows may comprise all three functional elements: vibratable member, return force component, and occlusion impact element. Preferably, the distal bellows has a diameter that is the same as the diameter of the catheter, and thus may supplant the distal-most aspect of the catheter head.

The hydraulic lumen comprising a distal bellows and proximal bellows may be designed to be used as a hydraulic catheter without a separate catheter housing. In a particular embodiment, the apparatus of the invention comprises a hydraulic catheter and a vibrational energy source operably connected to the hydraulic catheter, and the hydraulic catheter includes a hydraulic lumen having a proximal bellows as a proximal element, a distal bellows as a distal element, and a hydraulic tube sealingly connecting the proximal bellows to the distal bellows. The vibrational energy source is adapted to generate a plurality of hydraulic pressure waves into the hydraulic lumen via the proximal bellows, and each of the hydraulic pressure waves have at least one frequency and at least one amplitude, wherein the hydraulic tube is capable of transmitting the hydraulic pressure waves to the distal element (the distal bellows), and the distal element is capable of being energized by the plurality of hydraulic pressure waves to generate a vibration. In a particular embodiment, the system of the invention comprises the above apparatus and a control unit adapted to control the frequency and amplitude of hydraulic pressure waves generated by the vibrational energy source.

Optionally, additional return mechanisms may be used, for example, one or more springs, extensible lumen walls that are longitudinally elastic, or pulling wires which operate reciprocally with the hydraulic pressure pulse.

In another embodiment, an elastic membrane provides the functions of the vibratable member, return mechanism and occlusion impact element. The elastic membrane moves distally in response to hydraulic pulses in a hydraulic lumen of a catheter driving into the occlusion to impact and penetrate the occlusion. The elasticity of the elastic membrane also operates as a return force component to return the elastic membrane from an expanded state when the hydraulic pressure is removed. As an example, where the vibrational energy source is a solenoid that moves a mechanical plunger, the plunger may cause a proximal bellows or a proximal elastic membrane to expand and contract. The liquid inside the hydraulic lumen thereby can be made to move distally and proximally causing the elastic membrane at the distal end of the hydraulic lumen in turn to expand and contract. In particular, the apparatus comprises a hydraulic catheter and a vibrational energy source operably connected to said hydraulic catheter; the hydraulic catheter includes a hydraulic lumen having a proximal element, a distal element, and a hydraulic tube sealingly connecting the proximal element to the distal element. The vibrational energy source is adapted to generate a plurality of hydraulic pressure waves into the hydraulic lumen via said proximal element, and each of the hydraulic pressure waves have at least one frequency and at least one amplitude, wherein the hydraulic tube is capable of transmitting the hydraulic pressure waves to the distal element (the elastic membrane), and the distal element is capable of being energized by the plurality of hydraulic pressure waves to generate a vibration. The system comprises the above apparatus and a control unit adapted to control the vibrational energy source.

In still another embodiment, the vibratable member may be a guide wire. In this embodiment, the catheter may comprise a pair of hydraulic lumens that each possess expandable membranes as distal element, which expandable membranes cooperate to vibrate the distal portion of the guide wire, so that the distal tip (the impact end) of the guide wire oscillates at a frequency and amplitude sufficient to penetrate a blood vessel occlusion. In particular, the apparatus comprises a hydraulic catheter and a vibrational energy source operably connected to said hydraulic catheter. The hydraulic catheter includes a first hydraulic lumen having a first proximal element, a first distal element and a first hydraulic tube sealingly connecting the first proximal element and the first distal element; a second hydraulic lumen having a second proximal element, a second distal element, and a second hydraulic tube, wherein said second hydraulic tube sealingly connects said second proximal element to said second distal element; and a vibratable member. Preferably, the first distal element is a first expandable membrane, and the second distal element is a second expandable membrane. The vibrational energy source is adapted to generate a plurality of first hydraulic pressure waves into the first hydraulic lumen to expand the first expandable membrane and a plurality of second hydraulic pressure waves into said second hydraulic lumen to expand the second expandable membrane, and the vibratable member is capable of being oscillated by alternating expansion of the first expandable membrane and the second expandable membrane. The vibratable member may be a guide wire capable of oscillating by being reversibly flexed, the guide wire having an impact end and the hydraulic catheter further including at least one guide wire anchoring device. The system includes the above apparatus and a control unit adapted to control the vibrational energy source.

The apparatus of the invention is compatible for use with a guide wire, whether the hydraulic lumen is used in conjunction with a standard catheter, in particular a vascular catheter or itself serves as the catheter. For example, both the elastic membrane embodiment and the distal bellows embodiment may accommodate the use of a guide wire, as the guide wire may run through the hydraulic lumen or may be outside the hydraulic lumen, as described in more detail below with reference to the drawings.

Occlusions, in particular vascular occlusions, tend to have non-uniform density and hardness. Penetrating harder parts of an occlusion requires a relatively larger force than what is necessary for softer parts of the occlusion. The system of the invention comprises a control unit that is capable of adjusting the force applied against the occlusion by adjusting frequency or by adjusting the amplitude of oscillation of the vibratable member at the behest of the physician or automatically.

The minimal force necessary to recanalize a path through an occlusion is realized by the combination of frequency and amplitude of vibration. Increasing the amplitude of vibration or increasing the frequency of vibration will increase the force. Decreasing the amplitude or frequency of vibration will decrease the force. Determining the appropriate force for a given occlusion may be done "by feel" by the physician operator, based on the physician's experience and diagnostic skill. The operator may adjust the vibration to provide an appropriate force to penetrate an occlusion, by manually adjusting the frequency and/or amplitude of vibration directly through the control unit. Alternatively, the apparatus of the invention may further comprise a tissue sensor designed to measure directly or indirectly the hardness or stiffness of the biological matter forming the occlusion, and the amplitude and/or frequency of vibration of the vibratable member may be adjusted based on feedback from the tissue sensor. In such embodiments, feedback from the tissue sensor to a processor in either the control unit or user input-output device (also referred to herein as an operator interface unit) may allow the frequency and/or amplitude of vibration may be adjusted automatically by the control unit or manually by the physician operator based on operator-readable output from the user input-output device, optionally further comprising a display screen. In embodiments in which the operator adjusts the vibrational energy source, the control unit or operator interface unit may comprise adjustor means, such as knobs, dials, buttons levers and the like that permit adjustment of the amplitude or frequency of the hydraulic pressure waves generated by the vibrational energy source, digitally or in analog, similar to a rheostat or potentiometer.

In embodiments where the apparatus of the invention comprises a tissue sensor, the tissue sensor may be located in the catheter head, at the distal end of the catheter or hydraulic lumen to directly measure the resistance the occlusion impact element encounters against the occlusion. Occlusion hardness may be determined by measuring how much the distal bellows expands. In one mode of operation for directly measuring occlusion hardness, the expected amplitude of oscillation may set by the operator, and if the bellows expands less than the set amount, the calculated difference provides a measure of how much more force is required to achieve the correct amplitude of oscillation. The hardness or stiffness of the occlusion also may be measured indirectly based on pressure in the hydraulic system. The greater the hardness of the occlusion material the more resistance will be encountered, which may cause pressure to build within the hydraulic system. In one mode of operation, the pressure in the distal bellows may be compared to that in the proximal bellows, and the pressure differential provides a measure of how much more energy is required to achieve the adequate force to penetrate the occlusion material. In an alternative mode of operation, the tissue sensor may be located anywhere along the hydraulic lumen and pressure changes within the hydraulic lumen may be used to calculate indirectly hardness or stiffness of the occlusion. In any of these modes of operation, the tissue sensor may provide feedback to a processor that generates a readable output for the operator who can manually adjust the energy pulse input and subsequent hydraulic energy force through a control unit. Alternatively, the tissue sensor may provide feedback directly to the control unit that can be made to adjust the energy pulse input automatically.

The tissue sensor may be, for example, a strain gauge sensor, a piezoresistor, or a microstrain sensor. A strain gauge is a device used to measure deformation (strain) of an object. The most common type of strain gauge consists of an insulating flexible backing which supports a metallic foil pattern. The gauge is attached to the object by a suitable adhesive, such as cyanoacrylate. As the object is deformed, the foil is deformed, causing its electrical resistance to change. This resistance change, usually measured using a Wheatstone bridge, is related to the strain by the quantity known as a gauge factor. Commercial example of such a strain gauge that may be useful in the present invention is the Vishay 015DJ strain gauge (Vishay Intertechnology, Inc., Malvern, Pa., U.S.A.). A piezoresistor is a resistor made from a piezoresistive material having a sensitivity proportional to the piezoresistive gauge factor of the piezoresistor, which is defined by the relative change in resistance with strain. Silicon is a common material with which to form sensors comprising piezoresistors. Such piezoresistor sensors may comprise, for example, four 6-10 μm by 30-50 μm piezoresistors implanted in a high aspect-ratio cross-shape flexible element having a 525 μm high silicon mesa, as described in Beccai, L. et al., "Design and fabrication of a hybrid silicon three-axial force sensor for biomechanical applications," *Sensors and Actuators A: Physical*, Vol. 120, Issue 2, pp. 370-382, May 17, 2005. Piezoresistors are also described in U.S. Pat. Nos. 4,419,598 and 6,441,716, which are incorporated herein by reference; WO 2005/106417 describes strain sensors based on piezoresistor nanowires. Magnetoelastic sensors are low cost, miniature sensors with no moving parts, having other properties expected useful for biological applications. Magnetoelastic sensors are described in U.S. Pat. No. 7,062,981, which is incorporated herein by reference. Commercial examples of such magnetoelastic sensors that may be useful in the present invention are DVRT Microminiature Displacement Sensors (MicroStrain, Inc., Burlington, Vt., U.S.A.).

Without being bound by theory, the following explanation of one principle of operation of a tissue sensor according to the invention is provided. Young's Modulus is a measure of elasticity or the tensile properties of a solid object. It is determined by measuring the length or distance of perturbation of the object over a series of stress or pressure inputs. The harder the tissue, the more force is required to penetrate the tissue. An occlusion having a particular hardness or stiffness will have a particular Young's Modulus, which may be used to determine the force necessary to penetrate the occlusion. The force required to penetrate an occlusion may be estimated from Eq. 1:

$$F = ES\left(\frac{\Delta L}{L_0}\right), \tag{1}$$

where F is the force applied to the object, E is Young's Modulus, S is the original cross-sectional area through which the force is applied (i.e., the cross-sectional area of the probe or tissue sensor), $\Delta L$ is the amount by which the length of the object changes, and $L_o$ is the original length of the object.

To penetrate a distance $\Delta L$ into occlusion that comprises tissue having a Young's modulus of E and having geometrical dimensions L (length) with a probe having a cross-section S, a force F must be applied (Eq. 1). The greater the penetration distance $\Delta L$ intended, more force F needs to be applied. For the purposes of the present application it is useful to fix penetration distance $\Delta L$, and vary force F as function of the properties of the material.

Vibration is a regular periodic motion, having a peak acceleration ($a_{peak}$) that may be defined as set forth in Eq. 2:

$$a_{peak} = \omega^2 \Delta L = (2\pi f)^2 \Delta L \tag{2}$$

where $\omega$ is the angular frequency defined as $2\pi f$, and f is the frequency. As force (F) is a function of mass (m) and acceleration ($a_{peak}$), an applied force in vibration may be defined as set forth in Eq. 3:

$$F = ma_{peak} = m4\pi^2 \Delta L f^2 \tag{3}.$$

As Eq. 3 shows, force (F) is a function of frequency (f). In the hydraulic system of the invention, therefore, the frequency of the hydraulic pressure waves may be adjusted to achieve a force (i.e., excitation force or applied force) sufficient to penetrate the occlusion.

In order for an occlusion impact element to act with the same force on an object such as a vessel occlusion, which has non-uniform elastic properties (different Young's modulus), the frequency may be changed in accordance with Eq. 3. This is referred to hereinafter as a frequency-dependent vibration mechanism or frequency-modulation mechanism. Specifically, the working frequency may be changed (e.g., tuned, varied) in order to change (e.g., tune or vary) the excitation force. In other words, the frequency may be adjusted in order to obtain different intensities of applied force. Alternatively, the working amplitude of vibration may be changed without changing the frequency. To provide vibration force with particular frequency and amplitude, the vibratable member requires an excitation signal with a chosen frequency and amplitude. Changing signal frequency produces a frequency-modulated signal, whereas changing amplitude produces an amplitude-modulated signal. As an example, if m=1 gram, the vessel occlusion L=40 mm, the hydraulic catheter internal radius=4 mm, and the occlusion impact element S=0.5 mm$^2$, then assuming linear displacement is the same for all Young Modulus, the hardness or stiffness of the occlusion would be expected to vary from 10 MPa to 1 GPa. Biological material that makes up a vascular occlusion is expected to be linear over the small strains expected in the embodiments of the invention.

The apparatus of the invention may optionally comprise an anchoring element that secures the catheter to the walls of the blood vessel to improve vibration force delivery. These and other embodiments are described in detail below with reference to the drawings. The drawings, which are schematic and not necessarily to scale, are provided to depict selected embodiments and are not intended to limit the scope of the invention.

Figure 1B:
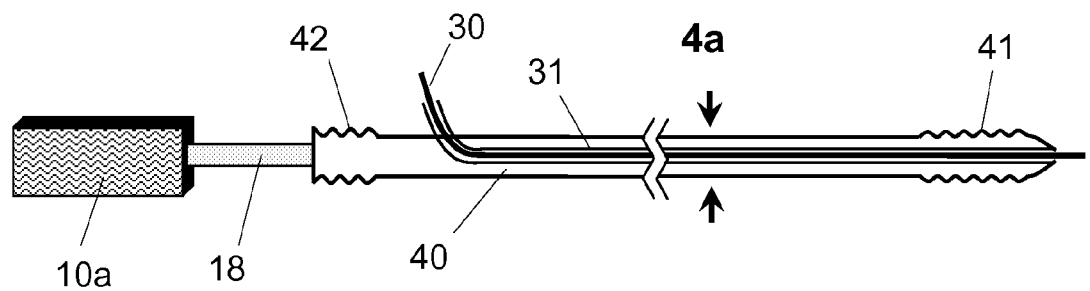
FIG. 1B illustrates a cut-away view to exemplify details of a hydraulic catheter.

FIG. 1 depicts elements of a system of the invention. In particular, FIG. 1A shows an apparatus, which comprises a hydraulic catheter 20 and active handle 14, a vibrational energy source 10 capable of generating a plurality of hydraulic pressure waves having at least one of a plurality of frequencies, and a control unit 11 capable of changing (adjusting) said frequencies. An optional operator interface unit 12, that may further comprise a display unit 13 is also shown. The hydraulic catheter 20 may be a conventional catheter that comprises a hydraulic lumen, or it may be a hydraulic lumen that itself may be used as a catheter, each of which types of embodiments are described below. Thus, the term "hydraulic catheter" is used herein to mean either a hydraulic lumen that may also function as a catheter or a catheter—conventional or otherwise—that contains a hydraulic lumen. The hydraulic catheter 20 has a proximal end 21 and a distal end 22, a catheter head 23 and a plurality of lumens therebetween (not shown) at least one of which is a hydraulic lumen. The term "catheter head" is used herein to mean the portion of the hydraulic catheter that contains the vibration member, return force component and occlusion impact element. Preferably the vibrational energy source 10 is connected to the active handle 14 via a hydraulic line or a mechanical line. The active handle 14 may comprise a proximal bellows functionally connected to a mechanical line such as a mechanical plunger (not shown, see, e.g., FIG. 1B). The system optionally may further comprise an imaging system 16, preferably an ultrasound imaging system, and visualization elements to assist in guiding the apparatus to the desired location in the body lumen. Optionally, the hydraulic catheter 20 may comprise Luer ports 17 useful for intravascular procedures, for example for attachment of a syringe for flushing or an hemostasis valve. Preferably, the catheter head 23 further comprises a tissue sensor 25 for measuring occlusion hardness.

The hydraulic catheter 20 optionally may further comprise an imaging component, such as intravascular ultrasonic (IVUS), to assist the operator in determining the location of the catheter head 23 relative to the target occlusion or vessel walls during operation of the device. Preferably, the imaging component is connected to a separate imaging system 16, illustrated in FIG. 1A. Alternatively, the imaging component may be functionally connected (not shown) to the operator interface unit 12 or display unit 13. The control unit 11 (see FIG. 1A) or operator interface unit 12 may further comprise a processor comprising a computer and relevant software to process incoming information from a tissue sensor, as described below, or a visualization device.

The vibrational energy source 10, which may be a shaker, hydraulic solenoid or actuator, or any similar energy source, is capable of generating different frequencies and/or amplitudes of hydraulic pressure pulses into the hydraulic lumen 40 of the catheter. The particular frequency or amplitude at any given time is controlled by adjusting the vibrational energy input via the control unit 11, which may be adjusted manually by the operator directly via the control unit 11 or through the operator interface unit 12 based on the information displayed on the display unit 13 or automatically as described below. Preferably the operator is a physician or a suitably trained technical specialist.

Optionally, but preferably, the frequency and amplitude may be adjusted based on the hardness of the occlusion. In such an embodiment, a tissue sensor 25, which in this embodiment is located in the catheter head 23, may be used to measure the hardness of the occlusion and provide feedback information from the distal end 22 of the hydraulic catheter 20 regarding the hardness or stiffness of the target occlusion, as described elsewhere herein. Such a tissue sensor 25 may transmit hardness measurement information to a processor (not shown), such as a computer with appropriate software, which may be integrated into the operator interface unit 12. The processor translates the measurement information into operator-readable information indicative of occlusion hardness, e.g., numerical or verbal categories, color codes, or graphs, which may be displayed on the display unit 13, or sounds codes. The operator may then change the frequency or the amplitude in real time, using, for example, a dial or buttons (not shown) on the operator interface 12, which transmits the desired adjustments to the control unit 11. In an alternative embodiment, the measurement information from the tissue sensor may be fed directly to the control unit 11, which can be designed to respond automatically to adjust the frequency and/or amplitude in conjunction with a processing unit (not shown), such as a computer with appropriate software, which may be integrated into the control unit 11. In a further alternative embodiment, the control unit 11 can be used to modulate the frequency and/or amplitude to predefined values or within a predefined range.

More particular aspects of an apparatus according to the invention is depicted in FIG. 1B. The apparatus of FIG. 1B comprises a hydraulic lumen 40 comprising a distal active bellows 41, a proximal bellows 42 and a vibrational energy source comprising a vibrational shaker 10a and a mechanical plunger 18. The proximal bellows 42 in the embodiment of FIG. 1B is functionally connected to the vibrational shaker 10a via a mechanical plunger 18. The vibrational shaker 10a may move the mechanical plunger 18 which in turn delivers to the proximal bellows 42 at least one energy pulse to the proximal bellows 42, contracting the proximal bellows 42 to generate a hydraulic wave that moves distally through the hydraulic lumen 40 causing the distal bellows 41 to expand. As the distal bellows 42 intrinsically comprises a spring mechanism, when force from the mechanical plunger 18 is removed from the proximal bellows 42, the expansion of the distal bellows 41 will subside, allowing the bellows to contract and return the hydraulic pressure pulse proximally. Where the mechanical plunger 18 is secured to the proximal bellows 42, the mechanical plunger 18 may be made to contract and expand the proximal bellows. The liquid inside the hydraulic lumen 40 thereby can be made to move distally and proximally causing the distal bellows 42 in turn to expand and contract. In either arrangement, the distal bellows 41 is made to oscillate at a frequency and amplitude determined by the input from the vibrational shaker 10a via the mechanical plunger 18. The frequency and amplitude of oscillation of the distal bellows 41 may be controlled via a control unit (not shown, see FIG. 1A). In alternative embodiments (not shown), a sealed plunger may deliver the hydraulic pressure pulse or a plunger can push a proximal diaphragm to initiate the hydraulic pressure pulse.

As further illustrated in FIG. 1B, a guide wire lumen 31 for housing a guide wire 30 is also provided. In embodiments such as this, where the guide wire and guide wire lumen are positioned inside the hydraulic lumen, diameters of these structures may, for example, be 0.014 inches (guide wire), 0.016 inches (guide wire lumen), and 0.04 inches (hydraulic lumen), but actual diameters may vary within ranges known to the skilled artisan. In such embodiments, the guide wire lumen will deviate from the hydraulic lumen to permit standard catheter-guide wire mounting such as "over the wire" or "rapid exchange". Thus, as illustrated in FIG. 1B, a guide wire lumen 31 that runs inside the hydraulic lumen 40 may exit through a port proximally, usually near the active handle, permitting the guide wire 30 to be inserted into or removed from the hydraulic lumen as needed.

Various exemplary embodiments of the apparatus of the invention or components of the apparatus of the invention are described below with reference to FIGS. 2-9.

Figure 2A:
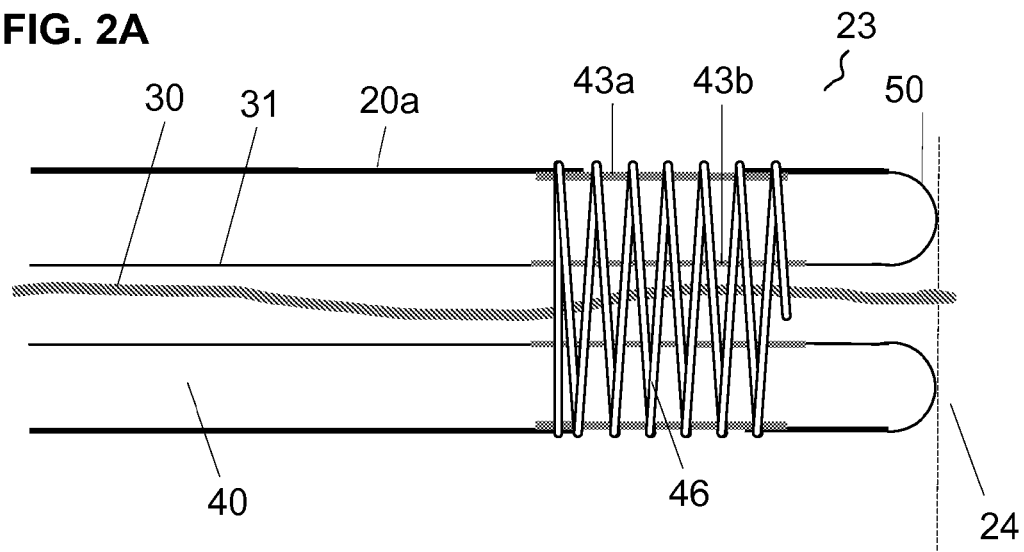
FIG. 2A illustrates a cut-away view of an embodiment of a distal element comprising a spring, an extensible housing and extensible interior lumen under conditions of lower hydraulic pressure
Figure 2B:
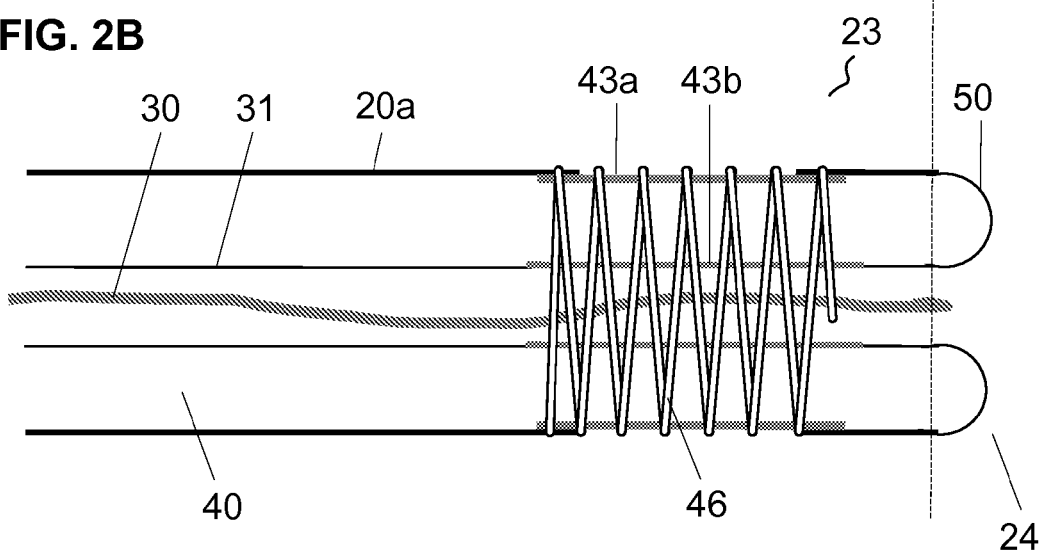
FIG. 2B illustrates a cut-away view of the same distal element embodiment under conditions of higher hydraulic pressure.
Figure 2C:
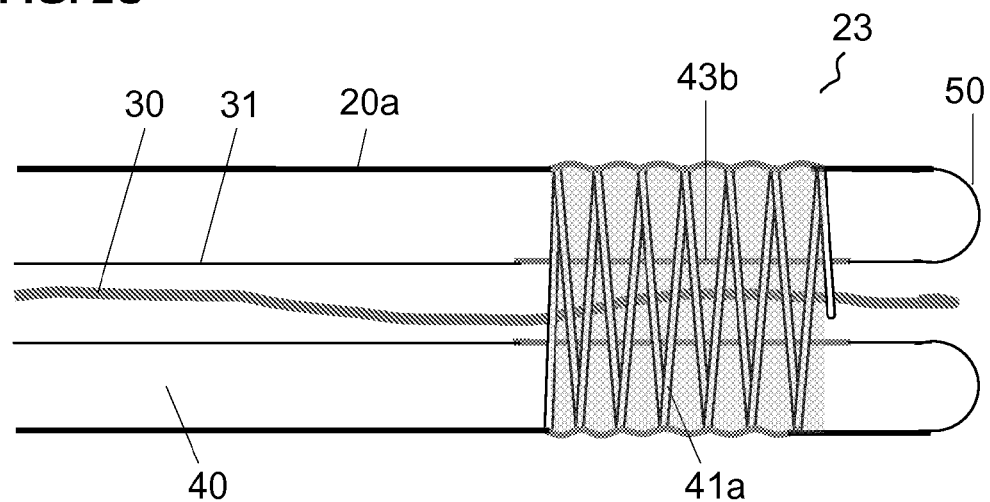
FIG. 2C illustrates a cut-away view of an embodiment of a distal element comprising a spring embedded in an extensible housing.

More particular aspects of embodiments of an apparatus according to the invention are depicted in FIGS. 2A-2C. Specifically, FIGS. 2A and 2B show an embodiment of the catheter head 23, illustrating a distal element comprising a spring 46, hydraulic lumen 40, and guide wire lumen 31. A guide wire 30 is shown in the guide wire lumen 31. In this embodiment, the distal element may be an open design spring-type structure that is housed in a compliant structure or covered by, or embedded in, a compliant material. The spring 46 may provide radial strength and limit radial expansion of the compliant structure or material. The compliant structure or material is extensible, i.e., it is capable of expanding and contracting in the longitudinal direction relative to the hydraulic catheter to accommodate expansion and contraction (vibration) of the bellows or spring in response to hydraulic pressure pulses), i.e., extensible. This property of longitudinal extensibility provides a localized compression-extension region of the hydraulic catheter so that only a small distal part of the hydraulic catheter will vibrate in response to the hydraulic pressure pulses. At the distal tip 24 of the catheter head is a penetration cap (impact end) 50 which functions as the occlusion impact element in this embodiment and may be connected to the spring 46 or to a non-compliant portion of the hydraulic catheter or hydraulic lumen.

The distal element depicted in FIGS. 2A and 2B has an extensible housing 43a as well as an interior extensible lumen wall 43b that defines an extension lumen to accommodate the guide wire 30. FIG. 2A depicts the spring 46 of the distal element where the hydraulic pressure is lower, and FIG. 2B depicts the spring 46 of the distal element where the hydraulic pressure is higher. The vertical dashed line extending from FIG. 2A to FIG. 2B serves to illustrate the relative position (not drawn to scale) of the catheter head distal tip 24 at the two relative hydraulic pressures. The spring 46 may provide a return force in this embodiment, but itself is not necessarily part of the sealed hydraulic lumen structure. In the embodiment of FIGS. 2A and 2B, the extensible housing 43a is shown as a polymeric material on the interior of the spring 46, however it may be placed on the exterior of the spring 46. In either case, the extensible housing 43a and the spring 46 may be affixed together or independently to the hydraulic lumen 20a, which is non-compliant. For extensible housing 43a made of material that is compliant in all directions, the extensible housing 43a is preferably positioned inside the spring 46 so that the spring 46 may serve to limit radial expansion of the material, allowing the compliant material to expand only longitudinally. Alternatively, as illustrated in FIG. 2C, a distal element may comprise a spring-bellows 41a, which comprises a spring embedded in a compliant polymeric material 43. The spring-bellows 41a may also be made by sealingly covering a spring with a thermoplastic material, such as a thin polyurethane, for example by evaporation methods. In the embodiment depicted in FIG. 2C, the spring-bellows 41a forms an integral part of the sealed structure of the hydraulic lumen.

The extensible housing 43a, extensible interior lumen wall 43b, and spring-bellows 41a comprise materials that are compliant under pressure, and therefore differ from the walls of the hydraulic lumen, catheter or guide wire lumen of the apparatus, which are flexible for maneuvering through body lumens but are non-compliant under pressure. The material used to cover or embed the springs illustrated in FIGS. 2A-2C preferably is a low durometer (shore)—i.e., highly stretchable—polymeric material. Examples of such highly stretchable polymeric materials include, but are not limited to, Pebax 25D, Hytrel (40D or lower), polyurethane 80A, rubber, latex or similar biocompatible materials. Similar materials may be used for the interior extensible lumen 43b. By contrast, the catheter wall 20a or wall of the guide wire lumen 31 are constructed of a higher shore material such as Pebax 7233, nylon 11, nylon 12, or other materials known in the art having comparable durometer. The extensible housing 43a (or the spring bellows 41a) and the interior lumen wall 43b are functionally and sealingly connected to the hydraulic catheter 20a and guide wire lumen 31, respectively, by means known in the art, for example by gluing or fusing.

Other distal bellows structures that include a housing and an interior lumen wall that are extensible also may be used in the apparatus of the invention. A distal element with these extensible features may be used in other embodiments of the apparatus of the invention, for example as described in FIGS. 3 and 5.

Figure 3A:
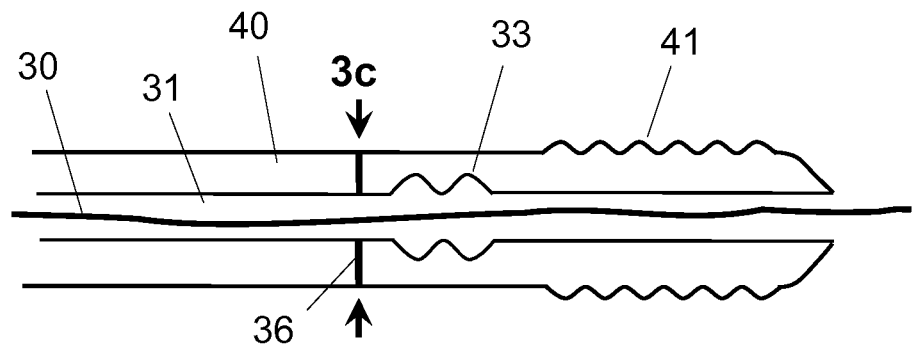
FIG. 3A illustrates a cut-away view of details of the distal end the hydraulic catheter comprising a distal bellows that is not expanded.
Figure 3B:
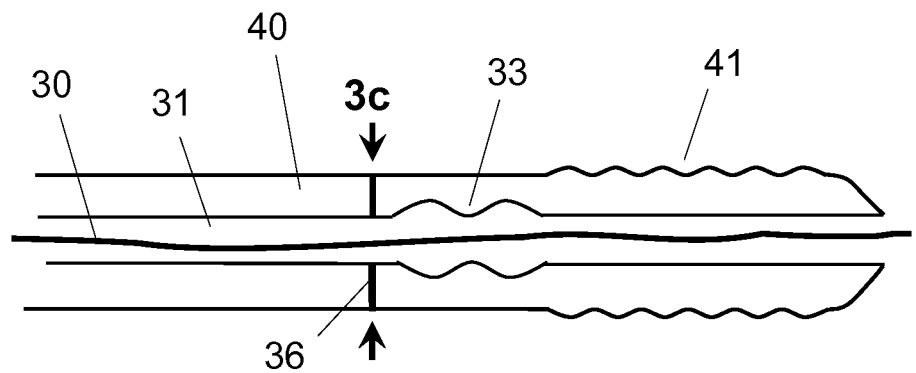
FIG. 3B illustrates details of the distal end of the same hydraulic catheter, where the distal bellows is in an expanded state.
Figure 3C:
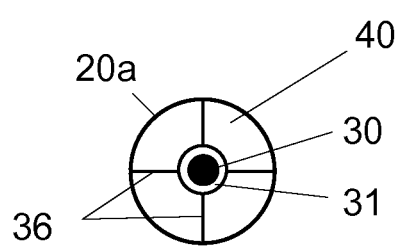
FIG. 3C provides a cross-section view of the hydraulic lumen of FIGS. 3A and 3B at position 3c, proximal of an extensible section of the guide wire lumen.

Optionally, the guide wire lumen 31 may have an extensible section outside the distal element. As illustrated in FIGS. 3A-3C, the guide wire lumen 31 may be affixed to the catheter wall 20a, i.e., the wall of the hydraulic lumen 40, close to the distal bellows by a plurality of guide wire lumen attachment elements 36 and include an extensible section. Whereas the guide wire 30 preferably is freely moveable within the guide wire lumen 31, the guide wire lumen 31 preferably is affixed to the distal bellows 41. Because the guide wire lumen 31 is connected to the distal bellows 41, it will move with the distal bellows. Accordingly, in this embodiment, the guide wire lumen 31 comprises an extensible section 33, as illustrated in FIGS. 3A and 3B. Preferably the extensible section 33 comprises a section of the guide wire lumen 31 that is elastic in the longitudinal direction relative to the hydraulic catheter. Materials suitable for the extensible section are similar to those described above for the extensible housing and interior lumen wall of the distal element of FIGS. 2A-C. One extensible section 33 is shown in FIGS. 3A and 3B, but the guide wire lumen 31 may comprise one or more extensible sections 33. The extensible section 33 is preferably located distal of a point where the guide wire lumen 31 is secured to the wall of the hydraulic lumen 40 (hydraulic catheter wall), indicated as 3c in FIGS. 3A and 3B. The one or more extensible sections 33 of the guide wire lumen 31—in combination with the guide wire lumen attachment elements 36—permit the guide wire lumen 31 to accommodate the oscillation of the distal bellows 41, while permitting the guide wire 30 to sit freely but relatively stationary within the guide wire lumen 31. This is illustrated in FIGS. 3A and 3B, as well as in FIG. 3C.

FIG. 3A illustrates the relative positions of distal bellows 41, guide wire 30, guide wire lumen 31 and guide wire lumen attachment elements 36 when the distal bellows 41 are in an unexpanded state; the extensible section 33 also is in an unexpanded state. By comparison, FIG. 3B illustrates the relative positions of distal bellows 41, guide wire 30, guide wire lumen 31 and guide wire lumen attachment elements 36 when the distal bellows 41 are in an expanded state; the guide wire extensible section 33 also is in an expanded state. The guide wire lumen attachment elements 36 effectively permit the guide wire lumen 31 to be divided into two sections, so that only the shorter distal section of the guide wire lumen 31 will vibrate. The extensible section 33 may comprise an elastic material or may comprise a spring and thereby function as a return force component in conjunction with the distal bellows 41. The guide wire lumen 31 of any embodiment in which the guide wire is not involved as a vibratable member, return force component or occlusion impact element may, in accordance with the invention, comprise one or more extensible sections 33.

FIG. 3C depicts a cross-section through point 3c in FIGS. 3A and 3B to show the plurality of guide wire lumen attachment elements 36 for this embodiment. Preferably, as illustrated by comparing FIG. 3C to, e.g., FIG. 3A, the guide wire lumen attachment elements 36 may be wider in the proximal-distal aspect (FIG. 3A) than in the radial aspect (FIG. 3C) to provide adequate support against the hydraulic pressure pulses without significantly affecting the movement of the liquid within the hydraulic lumen 40. The guide wire lumen attachment elements 36 provide stability for the guide wire lumen 31 during operation of the apparatus, i.e., when the vibratable member, in this case the distal active bellows 41, is oscillating. Preferably, the guide wire lumen attachment elements 36 are located close to the distal end of the hydraulic catheter, e.g., within 1-2 mm of the distal bellows 41.

The embodiments depicted in FIGS. 2A-2C, as well as other embodiments described below, also may optionally include a guide wire lumen 31 affixed to the catheter wall 20a and an extensible section 33, as described above for FIGS. 3A-3C.

In the embodiments of FIGS. 2 and 3, and optionally in other embodiments as will be appreciated by one skilled in the art, the guide wire lumen 31 may also function as a lumen for a visualization or imaging component—such as IVUS, optical coherence reflectometry (OCR) or Doppler ultrasound—or other useful or therapeutic component. In particular, the guide wire 30 may be removed from the guide wire lumen 31 when not needed, and replaced by a visualization component, i.e., the visualization component may be inserted into the same lumen 31 that previously housed the guide wire 30. Such visualization or imaging components may be useful during operation of the apparatus to properly position the catheter head relative to the occlusion and guide the vibratable member and occlusion impact element away from body lumen walls during operation. The term "lumen" is used herein to describe a tube-like structure—for example, a tubular structure in the body, such as a blood vessel, or a tubular structure of the apparatus of the invention, such as a hydraulic lumen or guide wire lumen. Accordingly, the term "lumen" includes the structure that is the tube per se—i.e., it refers to the lumen walls as well as the space therebetween as delineated by the walls.

Figure 4A:
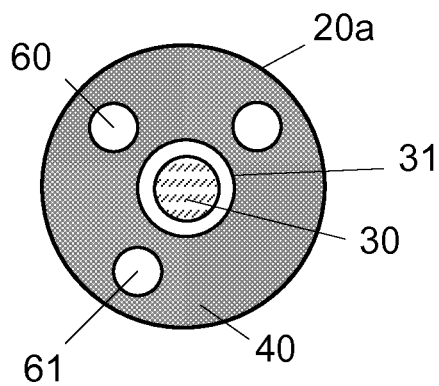
FIG. 4A illustrates a cross-section through an embodiment of a hydraulic catheter, such as the embodiment depicted in FIG. 1B, where the catheter lumen serves as the hydraulic lumen.
Figure 4B:
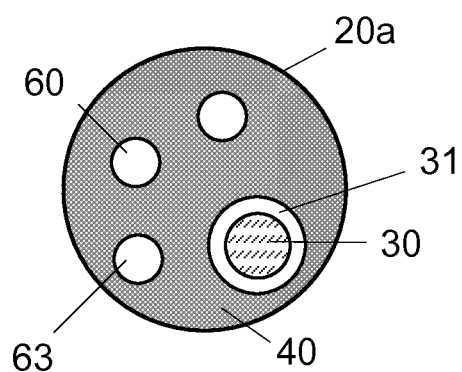
FIG. 4B illustrates a cross-section through another embodiment of a hydraulic catheter, where the catheter lumen serves as the hydraulic lumen, but the guide wire and guide wire lumen are not in the center of the hydraulic lumen.
Figure 4C:
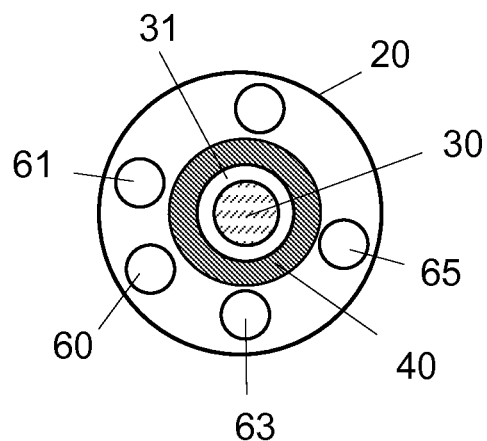
FIG. 4C illustrates a cross-section through one embodiment of a hydraulic catheter, such as that depicted in FIG. 5B (below), where the hydraulic lumen lies within a catheter lumen and comprises a guide wire lumen and guide wire.
Figure 4D:
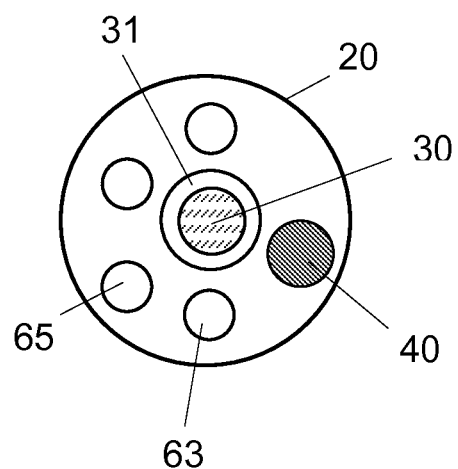
FIG. 4D illustrates a cross-section through another hydraulic catheter embodiment, such as that depicted in FIG. 6A (below), where the hydraulic lumen lies within a catheter lumen but does not comprise a guide wire lumen.

FIGS. 4A-4D are cross-sectional views through exemplary embodiments of the apparatus of the invention to further schematically illustrate aspects of the hydraulic catheter. FIG. 4A depicts more particular aspects of the hydraulic lumen 40 at point 4a of FIG. 1B. FIG. 4A also might reasonably depict a cross-section through the embodiments depicted in FIGS. 2, 3, and 5B. The guide wire lumen 31 and guide wire 30 are located approximately in the center of the hydraulic lumen 40. The outer wall of the hydraulic lumen 40 is indicated as hydraulic catheter 20a because in these embodiments the hydraulic lumen 40 is also a catheter. FIG. 4B illustrates a cross-section through an alternative embodiment of a hydraulic catheter according to the invention, showing that the guide wire 30 and guide wire lumen 31 may be positioned off-center within the hydraulic lumen 40. FIG. 4B might reasonably depict a cross-section through, for example, the embodiment illustrated in FIG. 5A. FIGS. 4C and 4D illustrate cross-sectional views through two exemplary embodiments comprising a catheter 20 that houses a hydraulic lumen 40. Specifically, in the embodiment depicted in FIG. 4C, the catheter 20 comprises a guide wire lumen 31, through which a guide wire 30 is inserted, which guide wire lumen 31, is located within a hydraulic lumen 40, consistent with, for example, a catheter comprising the hydraulic lumen embodiment depicted in FIG. 6B. Another arrangement is illustrated in FIG. 4D: the catheter 20 comprises a centrally located guide wire lumen 31, through which a guide wire 30 is inserted, and a hydraulic lumen 40, in which the liquid of the hydraulic system resides, which hydraulic lumen 40 lies parallel to the guide wire lumen 31. The embodiment depicted in FIG. 4D might reasonably depict a cross-section through a catheter comprising the hydraulic lumen embodiment illustrated in FIG. 6A.

The hydraulic catheter may include additional lumens, either within the hydraulic catheter, whether within the catheter 20 or within the hydraulic lumen 40, to permit inclusion of other features of the invention, or optional therapeutic or other useful components that the person having ordinary skill in the art may want to include for the PCI procedure. For example, FIGS. 4A and 4B show hydraulic lumens 40 that comprise additional lumens, indicated as 60, 61 and 63, and FIGS. 4C and 4D show catheters 20 that include additional lumens, indicated as 60, 61, 63 and 65. As described in the embodiments below, the hydraulic catheter may comprise lumens for any number of purposes. For example, the hydraulic catheter may include one or more lumens for housing various components within the scope of the invention, as are described in the various embodiments below, such as a tissue sensor; a guide wire anchoring device; a hydraulic catheter anchoring device; or a electrical energy supply. The lumen for a guide wire anchoring device or hydraulic catheter anchoring device may be an inflation lumen, where the anchoring device uses inflatable balloons. The catheter 20 or hydraulic lumen 40 may also comprise one or more lumens for optional components, such as a lumen for visualization or imaging component—for example, IVUS, OCR, Doppler ultrasound, fiber optics, or contrast agents, or an auxiliary lumen for housing such useful components as steering components or other therapeutic components. Thus, as illustrated in FIG. 4A-D, the hydraulic lumen 40 and catheter 20 variously may further comprise a lumen for a tissue sensor 60, a lumen for a hydraulic catheter anchoring device 61, a lumen for visualization components 63, and/or an auxiliary lumen 65. In some embodiments, one lumen may be used for more than one purpose. For example, a lumen may be designed to function as a guide wire lumen for insertion of the catheter into the body lumen, and then when the guide wire is not needed, it may be removed and the lumen may be used to deploy a visualization device for use during operation of the apparatus—e.g., penetration and traversal of an occlusion.

Figure 5A:
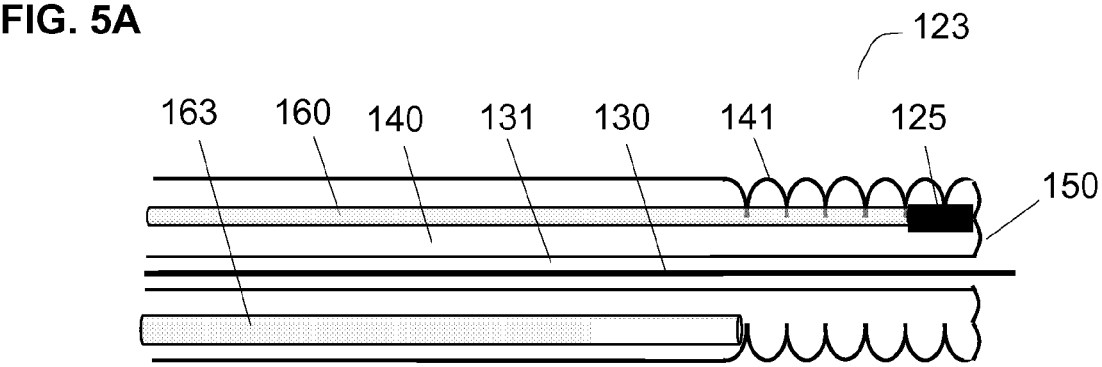
FIG. 5A illustrates a transverse view of one embodiment.
Figure 5B:
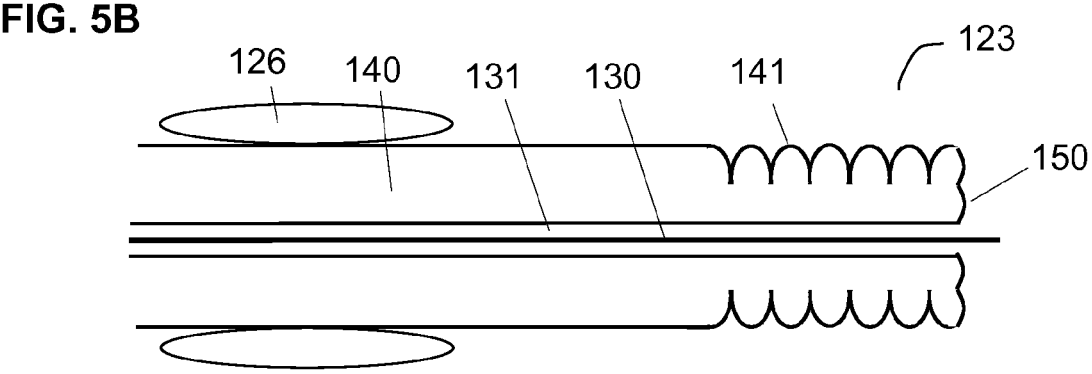
FIG. 5B illustrates a transverse view of another embodiment.

In one set of embodiments of an apparatus in accordance with the invention the vibratable member is a distal bellows 141, as depicted in FIGS. 5A and 5B. In these embodiments, the hydraulic lumen 140 comprises a proximal bellows 142 as a proximal element and a distal bellows 141 as a distal element. The hydraulic pressure pulse is generated by, for example, mechanical input to the proximal bellows, as depicted in FIG. 1B. The hydraulic pressure pulse travels through the hydraulic lumen to the distal bellows 141 to expand the distal bellows 141. In operation, the distal bellows 141 vibrates at a frequency and amplitude that is sufficient to penetrate a vessel occlusion. The distal bellows 141 is positioned at the most distal aspect of the apparatus and is the element that makes contact with the occlusion to be penetrated and traversed. Thus, the distal bellows 141 may have the function not only of vibratable member, but also return force component and occlusion impact element.

During operation, the guide wire 130 is retracted so as not to extend beyond the impact end 150 of the distal bellows 141. The distal end of the distal bellows 141 further may have an impact end 150, which functions as the occlusion impact element. The impact end 150 may be part of the bellows or independent structure attached to the bellows, and may be manufactured from suitable polymers or metals. When the distal bellows 141 has a closed bellows configuration, the impact end 150 may have a flat contour, however, whether it has a closed or open configuration, the distal bellows 141 may be fitted with a cap as an impact end 150, which cap may have any one of a number of surface contours, for example: flat, convex, low angle conical, or a plurality of nubs. FIGS. 5A and 5B depict an impact end 150 of the distal bellows 141 having a contour of a plurality of nubs. By comparison, the distal bellows of the embodiment of FIGS. 3A-3C is shown as a low angle conical contour.

More specifically, FIG. 5A depicts an embodiment in which the hydraulic lumen 140 comprises multiple lumens within it, including a guide wire lumen 131 to house a guide wire 130, a tissue sensor lumen 160 to service a tissue sensor 125, and a lumen for visualization (imaging) components 163. In this embodiment, the tissue sensor 125 is located on the distal bellows 141. The hydraulic lumen 140 of the embodiment depicted in FIG. 5B comprises a guide wire lumen 131 for housing a guide wire 130. Preferably, the hydraulic lumens depicted in FIGS. 5A and 5B are hydraulic catheters that may be deployed in a body lumen without a separate catheter housing. However, in alternative embodiments, the hydraulic lumens of FIGS. 5A and 5B may be used within a catheter—conventional or otherwise.

In any one of the embodiments of the invention, the apparatus may optionally include a hydraulic catheter anchoring device 126, as exemplified in FIG. 5B. The hydraulic catheter anchoring device 126 may be used to stabilize the hydraulic catheter within the body lumen during operation, so as to prevent substantial movement in response to the vibrational forces. The hydraulic catheter anchoring device 126 would be serviced by an anchoring device lumen (not shown; see, e.g., FIG. 4A). The hydraulic catheter anchoring device 126 may be, for example, one or more expandable balloons. In such an embodiment, the anchoring device lumen would be an inflation lumen filled with a fluid, preferably a liquid, more preferably a biologically compatible liquid, and used to inflate the hydraulic catheter anchoring device 126. As depicted in FIG. 5B, the hydraulic lumen 140 may carry one or more expandable balloons just proximal of the catheter head. In use, before energizing the hydraulic system, the one or more expandable balloons may be expanded, for example, to secure the hydraulic catheter in the blood vessel. It is expected that securing the hydraulic catheter in this manner will make the vibrational forces more effective in treating certain types of occlusions. In a similar manner, where the anchoring device may be used to secure the hydraulic lumen 141 within the catheter, it is expected to further stabilize the hydraulic lumen 141 and prevent it from moving substantially in response to the vibrational forces, making the vibrational forces more effective in treating certain types of occlusions.

Figure 6A:
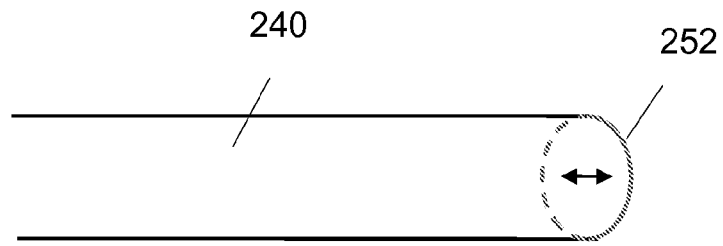
FIG. 6A illustrates an embodiment in which the hydraulic lumen does not also comprise a guide wire lumen.
Figure 6B:
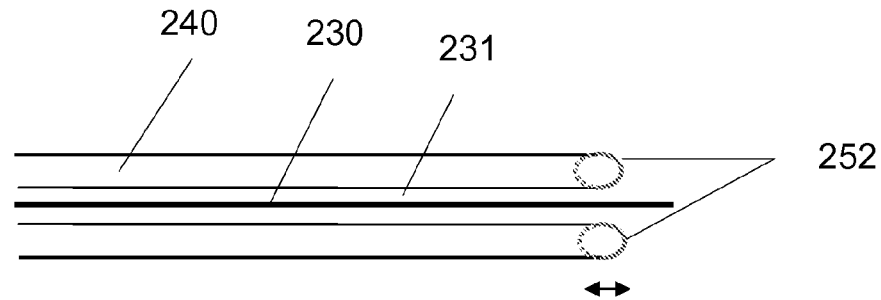
FIG. 6B illustrates an embodiment in which the hydraulic lumen comprises a guide wire lumen.

In other embodiments depicted in FIGS. 6A and 6B, the distal element of the hydraulic lumen 240 is an elastic membrane 252. In these embodiments, the elastic membrane 252 functions as a vibratable member, return force component, and occlusion impact element, although in other embodiments (not shown) the elastic membrane 252 may cause another structure to oscillate and impact an occlusion. In each of the FIG. 6A and FIG. 6B embodiments, the elastic membrane 252 is positioned at the distal end of a hydraulic lumen 240 and is sealingly attached thereto. The elastic membrane 252 may comprise a biologically compatible elastomer such as polyurethane, elastic silicon, or other biologically compatible elastic materials known in the art. The elastic membrane 252 of the embodiment depicted in FIG. 6A is shaped as a disk. The hydraulic lumen 240 of FIG. 6A may be used in a catheter (not shown) which catheter may comprise additional lumens, preferably running parallel to the hydraulic lumen, including a guide wire lumen for use with a guide wire. The hydraulic lumen 240 of the embodiment of FIG. 6B, by contrast, contains within it a guide wire lumen 231 for use with a guide wire 230. The guide wire 230 may be moved freely relative to the hydraulic lumen 240 and guide wire lumen 231, and may be removed if desired. The elastic membrane 252 of the embodiment of FIG. 6B is shaped as a "washer" or "ring", i.e., with a "hole" in the center to accommodate the guide wire 230. The elastic membrane 252 having a ring-shaped structure as in FIG. 6B provides both oscillation potential as a vibratable member and simultaneously positioning of the catheter over the guide wire 230. In either embodiment—that of FIG. 6A or 6B, the elastic membrane 252 at the distal end of the hydraulic lumen 240 would comprise the most distal aspect of the device so as to permit contact with the target surface, e.g., the surface of an occlusion, to effect penetration of the occlusion.

FIGS. 6A and 6B show the elastic membrane 252 at two extreme positions that may be achieved during operation; this is illustrative only and not meant to limit the positions of elastic membrane in any way. Hydraulic pressure pulses expand the elastic membrane 252 as shown by the solid line in FIGS. 6A and 6B. Between hydraulic pressure pulses (i.e., the interpulse phase) the elasticity of the elastic membrane 252 causes the elastic membrane 252 to retract, thereby operating as a return force component. The position of the elastic membrane 252 on expansion and retraction will depend on factors such as how the hydraulic system was designed (e.g., the liquid load), the amplitude of vibration, etc.; the elastic membrane 252 may retract to a "neutral" position, but it should expand to a position distal of the distal tip of the hydraulic tube. Optionally, if the applied hydraulic pressure is a sub-atmospheric pressure (which can occur if the system is so designed when the hydraulic liquid is added), the elastic membrane 252 may "retract" in a proximal direction to assume the other extreme position, depicted in FIGS. 6A and 6B as a dashed line.

Thus, in use, the hydraulic pressure causes expansion of the elastic membrane 252 and the elasticity of the elastic membrane 252 enables retraction causing the elastic membrane 252 to operate as a vibratable member that vibrates at a frequency and amplitude useful for penetrating an occlusion. The expanded elastic membrane 252 would contact the proximal surface of the occlusion being recanalized, thereby also functioning as an occlusion impact element. During operation of the apparatus depicted in FIG. 6B, the guide wire 230 is retracted so as not to extend beyond the distal end of hydraulic lumen 240 and elastic membrane 252. As the distal element of the hydraulic lumen 240, the elastic membrane 252 may operate in conjunction with a proximal element such as another elastic membrane (not shown) or a proximal bellows, as depicted, for example, in FIG. 1B. In either case, the proximal element of the hydraulic lumen is the portion of the hydraulic catheter operably connected to the vibrational energy source (not shown) of the apparatus.

Figure 7A:
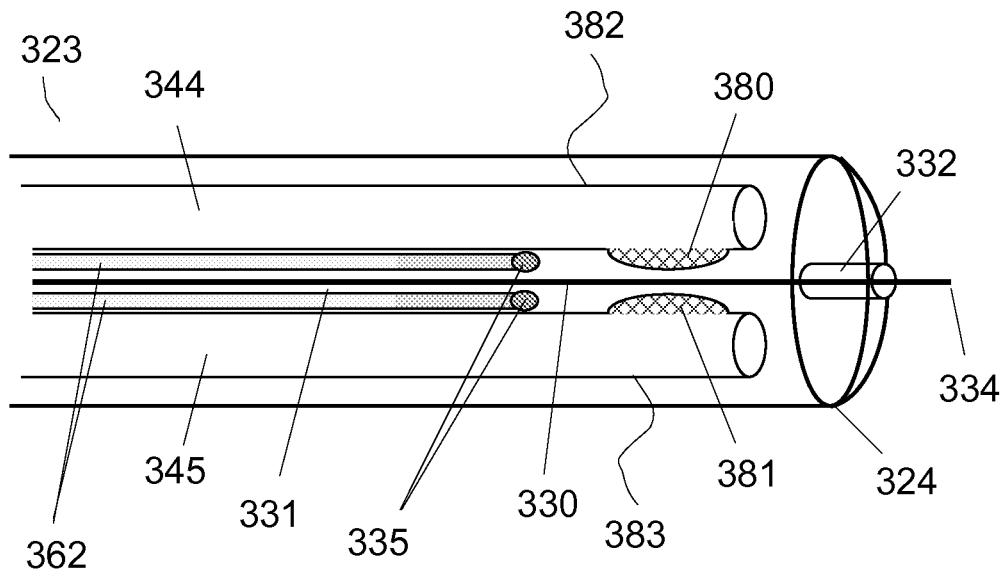
FIG. 7A is an axial cut-away view through the catheter head.
Figure 7B:
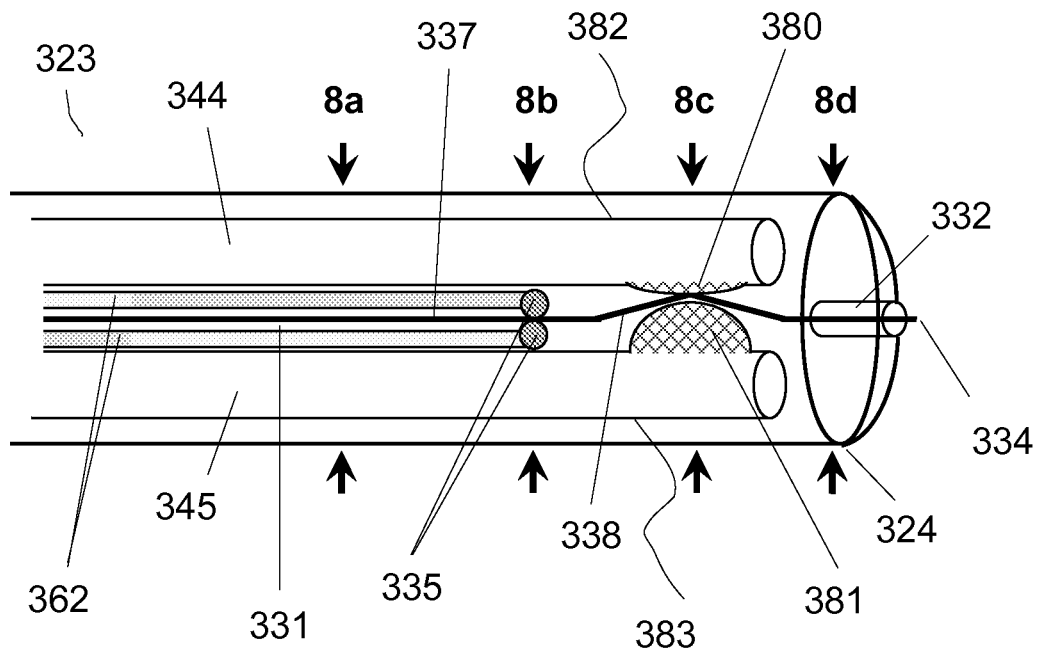
FIG. 7B illustrates an axial cut-away view through the catheter head of FIG. 7A showing the guide wire flexed by an expandable membrane.

Another embodiment of the apparatus of the invention is illustrated in FIGS. 7A and 7B. Cross-sections through this embodiment at positions 8A, 8B, 8C and 8D in FIG. 7B are depicted in FIGS. 8A, 8A', 8B, 8C, 8C', and 8D. In this embodiment, the apparatus comprises a hydraulic catheter that houses a dual lumen hydraulic system, which dual lumen hydraulic system comprises a first hydraulic lumen 344 and a second hydraulic lumen 345, and a vibrational energy source (not shown) operably connected to the hydraulic catheter. The first hydraulic lumen 344 has a proximal end (not shown) and a distal end 382. The distal end 382 of the first hydraulic lumen 344 comprises a functionally connected first expandable membrane 380 as a distal element of the hydraulic system. The second hydraulic lumen 345 has a proximal end (not shown) and a distal end 383. The distal end 383 of the second hydraulic lumen 345 comprises a functionally connected second expandable membrane 381 as a distal element of the hydraulic system, shown expanded in FIG. 7B. The first and second expandable membranes 380, 381 are located within the catheter head 323. The first and second hydraulic lumens 344, 345 function as inflation lumens for the first and second expandable membranes 380, 381, respectively. The vibrational energy source may generate hydraulic energy waves into the first hydraulic lumen via first proximal element and into the second hydraulic lumen via a second proximal element, which first and second proximal elements may be a bellows or an elastic membrane.

In use, hydraulic pressure is used to expand and contract the first and second expandable membranes 380, 381 via the first and second hydraulic lumens 344, 345. The first and second hydraulic lumens 344, 345 may be designed to have any of a variety cross-sectional shapes. Two such cross-sectional shapes are illustrated in FIGS. 8A and 8A': FIG. 8A illustrates a circular cross-section, FIG. 8A' illustrates a moon-shaped cross-section. FIGS. 8C and 8C' illustrate these two cross-sectional shapes when the second expandable membrane is inflated. The catheter of the embodiment of FIGS. 7A and 7B further comprises a guide wire lumen 331 for housing a guide wire and a guide wire short lumen 332 located at the distal-most part of the catheter head 323. The distal 2-5 cm of the guide wire is the vibratable portion 338 of the guide wire, which functions as the vibratable member in this embodiment and comprises an impact end 334 at its distal tip, which is the portion of the guide wire that would contact the occlusion during operation of the apparatus and therefore serves as the occlusion impact element. The distal elements of the hydraulic lumen 340 (the first and second expandable membranes 380, 381) operate to vibrate the vibratable portion 338 of the guide wire, as described below. The guide wire short lumen 332- to stabilize and center the vibratable portion 338 of the guide wire at its distal end, as described below—is further illustrated in FIG. 8D, which depicts a cross-section view through the catheter at position 8D of FIG. 7B.

To ensure that only the distal approximately 2-5 cm of the guide wire vibrates, the apparatus of this embodiment still further comprises one or more guide wire anchoring devices 335 and a lumen for the guide wire anchoring device 362. A pair of guide wire anchoring devices 335 is shown in FIGS. 7A and 7B. Said guide wire anchoring devices 335 are capable of functionally engaging the stationary portion 337 of the guide wire to fix its position relative to the first and second hydraulic lumens 344, 345 and catheter head 323, proximal of the first and second expandable membranes 380, 381. The function of the guide wire anchoring devices 336 is illustrated by comparing FIG. 8B, which depicts the position of the stationary portion 337 of the guide wire, to FIGS. 8C and 8C', which depict the vibratable portion 338 of the guide wire; cross hairs indicate the center of the hydraulic catheter 320. FIG. 8D illustrates how the guide wire short lumen 332 can limit the lateral movement of the distal end of the vibratable portion 338 of the guide wire to the center of the hydraulic catheter 320. The guide wire anchoring devices 335 preferably are positioned about 1-5 cm from the distal tip, or impact end 334, of the guide wire. The guide wire anchoring device 335 may be any anchoring device known to the skilled artisan, for example, an inflation balloon, in which case the lumen 362 for the guide wire anchoring device may be an inflation lumen, as depicted in FIGS. 7A and 7B. The lumen 362 for the inflation balloon anchoring device 335 may extend from a proximal end, where the inflation and deflation process is controlled, to a distal end, where the lumen 362 is sealingly connected to the inflation balloon anchoring devices 335. To inflate the inflation balloon guide wire anchoring devices 335, such an inflation lumen 362 preferably may be filled with an inflation fluid. In the embodiment depicted in FIGS. 7A and 7B, the guide wire lumen 331 ends at the point of the guide wire anchoring devices 335, as also illustrated by comparing FIGS. 8A and 8A', which depict cross-section views through the hydraulic catheter at position 8A of FIG. 7B, to FIG. 8B, which depicts a cross-section view through the hydraulic catheter at position 8B of FIG. 7B.

When the apparatus is not in use and during insertion of the apparatus into a body lumen, the one or more guide wire anchoring devices 335 do not engage the guide wire 330, so that the guide wire 330 may move freely relative to the catheter and first and second hydraulic lumens 344, 345. As illustrated in FIG. 7A, the pair of inflatable balloon-type guide wire anchoring devices 335 are in a deflated state (see also FIG. 8B). FIG. 7A further shows that, like the guide wire anchoring devices 335, the first and second expandable membranes 380, 381 also are in a deflated state when the apparatus is not in use or during insertion into a body lumen. In this configuration, the guide wire may be used to guide the catheter to the desired location within a body lumen. Further, the guide wire may be positioned relative to the catheter to be in contact with a target lesion. Preferably, the distal end 324 of the catheter is positioned between about parts of a mm (e.g., 100 µm) to about 10 mm from the impact end 334 of the guide wire. The hydraulic catheter and guide wire may be positioned relative to one another with the aid of radiopaque markers known in the art, e.g., using angiography.

Once the guide wire and hydraulic catheter are in position, the guide wire 330 may be secured by the one or more guide wire anchoring devices 335. In the embodiment depicted in FIGS. 7A-B and 8A-D, the lumen 362 for the guide wire anchoring devices is an inflation lumen which is pressurized with an inflation fluid, preferably a liquid, preferably the liquid is a biologically compatible liquid, to inflate the guide wire anchoring devices 335, which in this embodiment are inflatable balloons. The guide wire anchoring devices 335 thereby engage the stationary portion 337 of the guide wire and lock its position relative to the first and second hydraulic lumens 344, 345 and the catheter head 323. FIGS. 7B and 8B show the pair of inflatable balloon-type guide wire anchoring devices 335, inflated state to anchor the stationary portion 337 of the guide wire. Locking the guide wire in this fashion permits the distal elements of the hydraulic system to oscillate only the distal end of the guide wire, while the proximal portion of the guide wire remains steady, thereby defining the stationary portion 337 and vibratable portion 338 of the guide wire, as illustrated in FIG. 6B.

Specifically, the dual hydraulic lumen embodiment may function as follows: Operation of the apparatus involves a cyclical series of steps, wherein the hydraulic lumens 344, 345 are independently pressurized and depressurized 180 degrees out of phase to one another to alternately expand and contract the expandable membranes 380, 381 and thereby bend the vibratable portion 338 of the guide wire. Each of two phases of the cycle involves a pressurizing of one hydraulic lumen, and depressurizing of the other hydraulic lumen. To begin, the hydraulic system is charged, causing some hydraulic pressure in both the first and second hydraulic lumens 344, 345. The first phase of the cycle may begin with a pulse of positive pressure applied to the second hydraulic lumen 345 causing the second expandable membrane 381 to protrude radially from the second hydraulic lumen 345 thereby bending the guide wire, as illustrated in FIG. 7B. Simultaneously, the first hydraulic lumen 344 is put under sub-atmospheric pressure—so that the first expandable membrane is in a retracted position but is still capable of supporting the vibratable portion 338 of the guide wire. In the next part of this first phase of the cycle, the positive pressure to the second hydraulic lumen 345 is removed and positive pressure is applied to the first hydraulic lumen 344. During an interphase period, both the first and second expandable membranes 380, 381 achieve a neutral position relative to the vibratable portion 338 of the guide wire, which vibratable portion 338 straightens due to its intrinsic "elasticity."

The second phase may then begin, in which a pulse of positive pressure is applied to the first hydraulic lumen 344 causing the first expandable membrane 380 to protrude radially from the first hydraulic lumen 344, thereby bending the vibratable portion 338 of the guide wire in a direction opposite that in the first phase, and the second hydraulic lumen 345 is put under sub-atmospheric pressure causing the second expandable membrane 381 to retract but still support the guide wire. The cycle continues with the pressure in the first hydraulic lumen 344 decreasing toward atmospheric pressure and the pressure in the second hydraulic lumen 381 increasing toward atmospheric pressure toward a second interphase neutral state where the vibratable portion 338 of guide wire again straightens due to its intrinsic "elasticity." The cycle is repeated such that pressure in one hydraulic lumen is alternately higher than the pressure in the other hydraulic lumen, at a frequency sufficient to vibrate the guide wire at frequency sufficient to penetrate the occlusion.

Bending the vibratable portion 338 of the guide wire causes that region of the vibratable portion 338 of the guide wire within the supporting guide wire short lumen 332 to slide proximally, supported and centered by the guide wire short lumen 332, and the impact end 334 of the guide wire to move proximally. Therefore, when the vibratable portion 338 of the guide wire is bent, its effective length is shortened (compare FIG. 7A to FIG. 7B). The straightening of the vibratable portion 338 of the guide wire during the interphase period causes the impact end 334 to move distally, the guide wire short lumen 332 continuing to support and center the distal end of the vibratable portion 338 of the guide wire. The two-phase operation is continued in periodic fashion to provide periodic bending and straightening the vibratable portion 338 of the guide wire to cause the impact end 334 of the guide wire to oscillate in a proximal-distal direction and function as a drilling pin to penetrate an occlusion. The cycle of phase 1 and phase 2 is repeated until the proximal surface of the occlusion is penetrated. The apparatus is then advanced until a new proximal surface of the occlusion is contacted and the cycle is repeated.

Specifically, the invention encompasses a method of vibrating the guide wire of the apparatus of FIGS. 7A and 7B comprising the steps of: (a) locking said distal end of said guide wire relative to a remainder of said guide wire by engaging said at least one guide wire anchoring device; and (b) generating a plurality of first hydraulic pressure waves from said vibrational energy source into said first hydraulic lumen and a plurality of second hydraulic pressure waves from said vibrational energy source into said second hydraulic lumen, wherein said plurality of first hydraulic pressure waves are 180 degrees out of phase with said plurality of second hydraulic pressure waves. The invention further comprises a method of vibrating the guide wire of the apparatus of FIGS. 7A and 7B comprising the steps of: (a) locking said guide wire by engaging said guide wire anchoring devices; (b) effecting a positive hydraulic pressure pulse to said first hydraulic lumen and simultaneously releasing hydraulic pressure to said second hydraulic lumen; (c) effecting a positive hydraulic pressure pulse to said second hydraulic lumen and simultaneously releasing hydraulic pressure to said first hydraulic lumen; (d) repeating steps b-c to effect oscillation of said impact end of said guide wire at a predefined frequency and amplitude.

The invention also encompasses a method of penetrating an occlusion with the apparatus of FIGS. 7A and 7B comprising the steps of: (a) inserting into a body lumen or blood vessel the apparatus of FIGS. 7A and 7B, and advancing said apparatus until said impact end of said guide wire contacts a first proximal end of a vessel occlusion; (b) locking said guide wire by engaging said guide wire anchoring devices; (c) effecting a positive hydraulic pressure pulse to said first hydraulic lumen and simultaneously releasing hydraulic pressure to said second hydraulic lumen; (d) effecting a positive hydraulic pressure pulse to said second hydraulic lumen and simultaneously releasing hydraulic pressure to said first hydraulic lumen; (e) repeating steps c-d to effect oscillation of said impact end of said guide wire at a predefined frequency and amplitude until said first proximal surface of the occlusion contacted by the impact end of guide wire is penetrated; (f) advancing said catheter and guide wire until said impact end of said guide wire contacts a new proximal end of said occlusion; (g); repeating steps c-e until said occlusion is penetrated.

In this embodiment, the vibratable portion 338, which comprises the distal-most 2-5 cm of the guide wire 330, functions as a vibratable member, the impact end 334 functions as an occlusion impact element, and the flexibility of the guide wire functions as a return force component. As described above, the guide wire short lumen 332 located at the distal end 324 of the catheter provides a means to stabilize and center the vibratable portion 338 of the guide wire 330 at its distal end during operation, i.e., to minimize lateral movement of the impact end 334 of the guide wire. The frequency or amplitude of the positive hydraulic pulse in each hydraulic lumen may be adjusted manually or automatically, in a manner similar to that described previously for other embodiments. Preferably, the amplitude of vibration will be set to effect a longitudinal displacement of the impact end 334 of the guide wire of between about parts of a mm (e.g., about 100 μm) to several mm.

Figure 9A:
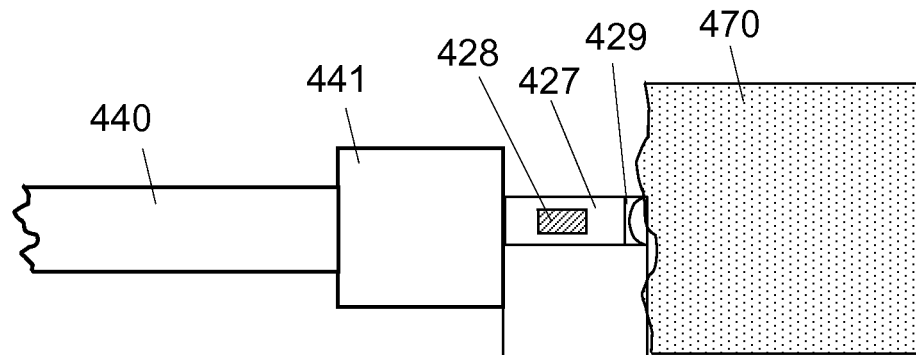
FIGS. 9A-9C illustrate how an embodiment of a tissue sensor attached to a distal bellows might be used to determine whether the appropriate force is applied to occlusions of differing hardness.
Figure 9B:
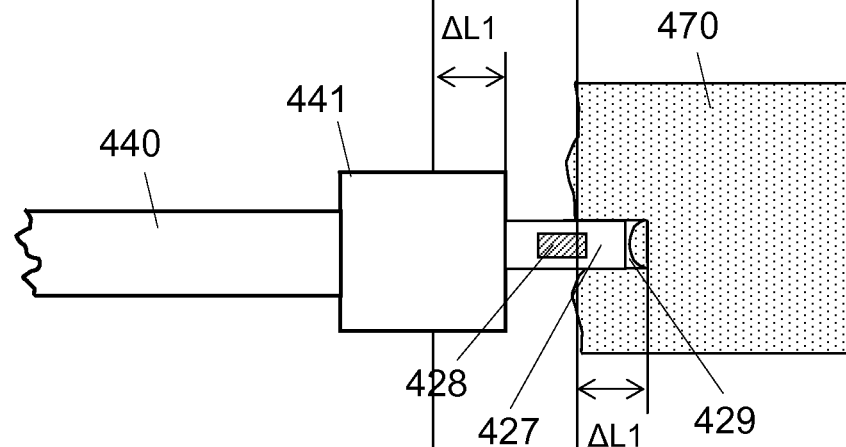
Figure 9C:
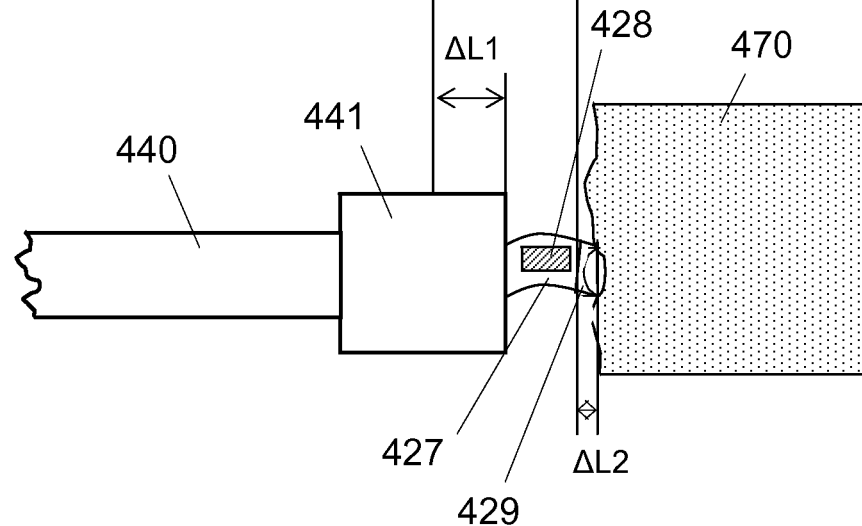
Figure 9D:
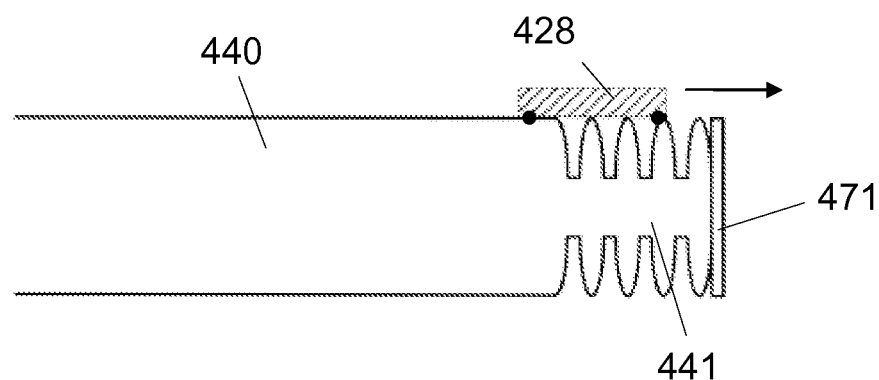
FIGS. 9D and 9E illustrate two ways a strain gauge sensor of a tissue sensor might be attached to a distal bellows.
Figure 9E:
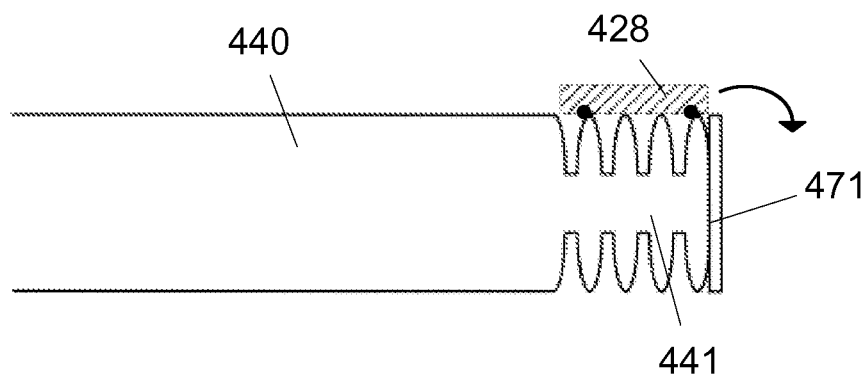

The apparatus of any embodiment of the invention may further comprise a tissue sensor for measuring the hardness of the occlusion to be penetrated. FIGS. 9A-E illustrate aspects of a tissue sensor and its operation with respect to the invention. In particular, FIGS. 9A-C illustrate one way to measure whether desired amplitude is achieved, using a tissue sensor comprising a probe, strain gauge and touch sensor. FIGS. 9D and 9E illustrate two types of strain gauges.

The system may be set by the operator to achieve desired displacement, or target penetration amplitude ($A_0$). The target amplitude, $A_0$, may not be achieved, however, if the applied force does not match the occlusion hardness, and the achieved amplitude (A) must be determined. The achieved amplitude, A, may be monitored via a tissue sensor in any one of several ways described below or that will become apparent to the person of ordinary skill in the art in view of the examples set forth below. For example, achieved amplitude, A, may be measured directly, for example using a strain gauge or by measuring displacement of either the proximal or distal bellows or both the proximal and distal bellows. In such embodiments, the tissue sensor may comprise a probe 427, strain gauge 428, and touch sensor 429, which, as depicted in FIGS. 9A-9C, measure occlusion hardness separate from stress on the vibratable member. Alternatively, the tissue sensor may comprise a strain gauge sensor 428 that may be attached directly to the vibratable member, as depicted for example in FIGS. 9D and 9E, to measure strain on the vibratable member. The achieved amplitude, A, also may be measured indirectly. As the apparatus comprises a hydraulic lumen, penetration amplitude may be determined by measuring pressure generated in the hydraulic system due to resistance against the occlusion.

Young's Modulus (E) may be estimated using Eq. 1 above. To define the mechanical properties of the occlusion tissue, so as to adjust the frequency and amplitude for penetration, two parameters should be monitored: force (F) and displacement (L). Of the other parameters of Eq. 1, S the cross-sectional area of the probe or sensor (which may be guide wire or other element with known dimensions), known, whereas L, the length of occlusion, is unknown. Nevertheless, the force required to penetrate a tissue of unknown hardness may be determined, as illustrated in FIGS. 9A-9C. The hydraulic lumen 440 (or hydraulic catheter) comprising a distal element 441 and tissue sensor is provided. The tissue sensor comprises a probe 427, a strain gauge 428, and a touch sensor 429. There are two modes in the working cycle, the measurement mode and the vibration mode. First in the sequence is the measurement, second in the sequence is vibration. In measurement mode, when the touch sensor 429 is placed close to occlusion 470 and touches it, as shown in FIG. 9A (a contact the physician-operator can feel), the measurement mode is switched on. Measurement mode is a single pulse mode, and the probe may penetrate into the occlusion.

In accordance with Eq. 3 above, the amount of force to apply is determined by displacement $\Delta L$ and frequency f. Fixing $\Delta L$ (stroke or amplitude of vibration) at a specific target value, for example, 0.1 mm for the constant liquid mass in hydraulic lumen (a value determined from a safety standpoint), force F may be changed by varying the frequency f. At the starting point, the force pulse is provided at a defined frequency f and amplitude A. FIG. 9B illustrates an applied force that is sufficient to penetrate the occlusion at the full depth $\Delta L$. That the target displacement as been achieved may be confirmed with strain gauge sensor, which may provide signals proportional to bending or strain of the probe. See FIGS. 9D and 9E. Practically, the catheter or hydraulic lumen 440 is unlikely to be completely straight, but rather may be curved or undulating due to the shape of the body lumen, especially in blood vessels. This means that the initial force provided by the vibrational energy source decreases somewhat, and cannot be taken at face value for an estimation of occlusion hardness. Moreover, the operator may push the catheter or hydraulic catheter with unknown force, which cannot be controlled or readily measured by the apparatus. In such circumstances, not only the occlusion length but also the actual applied force at the distal end is approximate. Nevertheless, under such conditions, estimation of occlusion tissue mechanical characteristics may be made in relative rather than absolute terms, i.e., values at the distal end can be calibrated from the values at the proximal end. If the initial inputted vibration force is $F_0$ with stroke (amplitude) $\Delta L_0$ at the proximal point, it will reach values $F_1$ and $\Delta L_1$ at the distal point. Thus, if the applied force is sufficient to penetrate into the occlusion tissue 470, the penetration depth will be almost the same as stroke value $\Delta L_1$ or amplitude as shown on FIG. 9B. By contrast, if the applied force is insufficient for full penetration, the probe 427 may bend, as illustrated in FIG. 9C, and the strain gauge sensor 428 may provide a corresponding signal. In this scenario, the applied force may be increased by changing its frequency (frequency-dependent vibration mechanism) or its amplitude (amplitude-dependent vibration mechanism).

FIGS. 9D and 9E illustrate how strain gauge sensors may be used in accordance with the invention. Strain gauges may be placed on the apparatus of the invention to assess resistance against a target in two modes. Longitudinal displacement and flexing displacement. FIG. 9D depicts a strain gauge sensor 428 attached to a distal element 441 of a hydraulic lumen 440, in this embodiment also a catheter, to measure longitudinal displacements without bending. Such displacements may arise from resistance against a target surface 471, such as the proximal surface of an occlusion. In such embodiments, the strain gauge 428 may be attached to the distal element of the hydraulic system and the hydraulic pipe of the hydraulic lumen to measure longitudinal displacement. Thus, as depicted in FIG. 9D, a strain gauge 428 is attached, as indicated by the black dots, to a distal element 441 and the wall of the hydraulic lumen 440 (hydraulic catheter). FIG. 9E depicts a strain gauge sensor 428 attached to a distal element of a hydraulic lumen to measure flexing of the distal element of the hydraulic lumen. Such flexing may arise from resistance against the target surface 471, such as the proximal surface of an occlusion. In such embodiments, the strain gauge 428 may be attached to two points on the distal element to measure flexion of the distal element. Thus, as depicted in FIG. 9E, a strain gauge 428 is attached, as indicated by the black dots, to two points on a distal element 441. Optimally, two strain gauges may be used to verify that displacement occurs in the longitudinal direction, for example one strain gauge may be attached to two points on a distal element as in FIG. 9E and a second strain gauge may be attached to the distal bellows and the wall of the hydraulic catheter.

Figure 10:
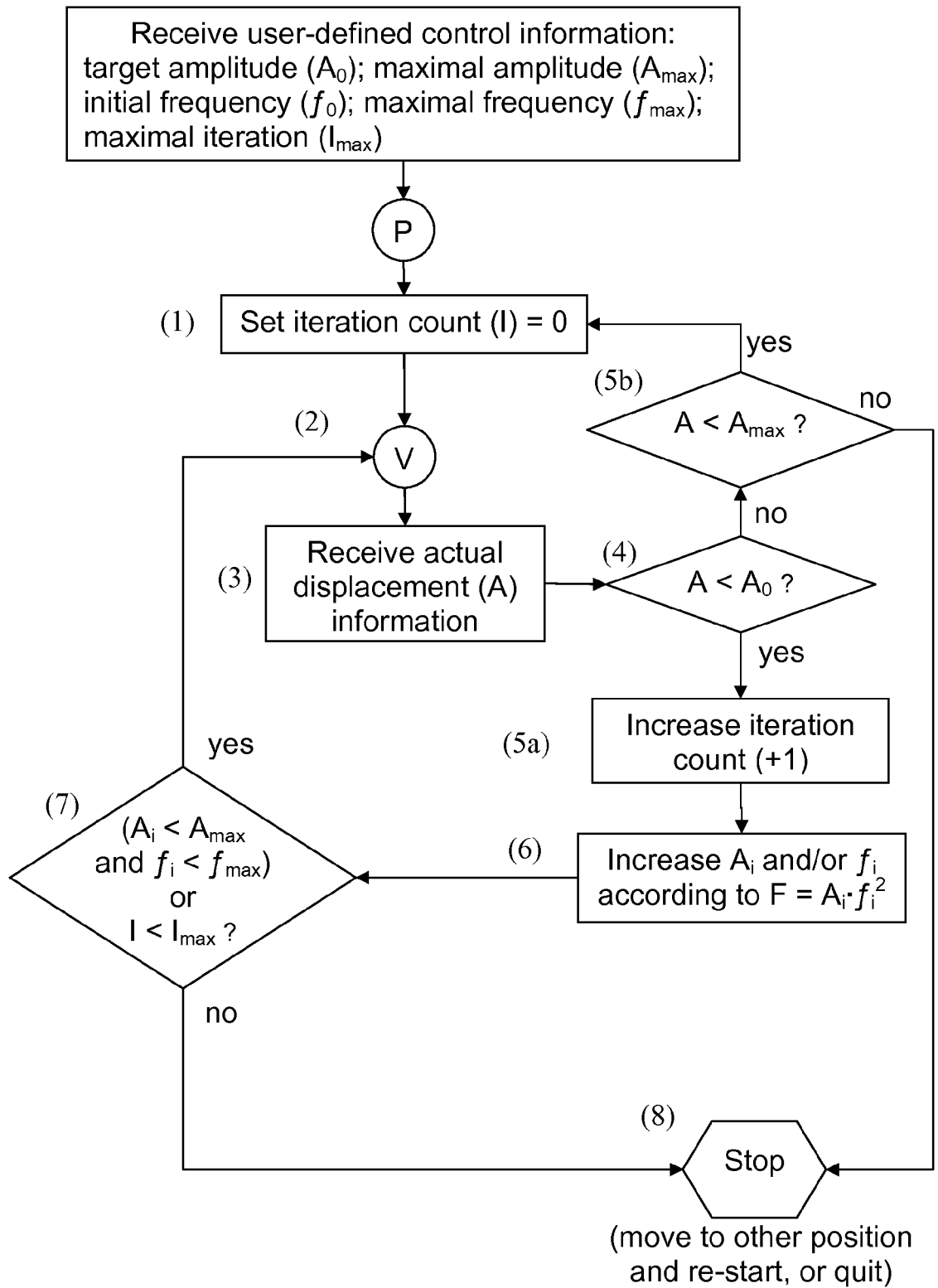
FIG. 10 illustrates one embodiment of a control scheme for adjusting the hydraulic energy input.

The invention encompasses a method of controlling the vibration force. FIG. 10 illustrates one way a control unit might be used in accordance with the invention to monitor penetration amplitude and adjust the amplitude of oscillation if necessary. Control of the frequency and amplitude of vibration is best understood in the context of penetrating an occlusion, such as a vascular occlusion. When the system of the invention is used to penetrate a vessel occlusion, complete penetration may occur over a series of penetration cycles in which frequency and a target amplitude are set prior to initiating vibration in the apparatus, and then adjusted by the control unit throughout the penetration cycle. Each penetration cycle may involve a series of vibration "cycles", in which the effectiveness of the vibration is periodically measured, and the force adjusted as necessary in a manner to maximize both safety and success of penetration. As discussed above, in one mode of operation, the desired penetration amplitude (stroke) may be set at a fixed distance. The control unit of the system of the invention may be used to monitor whether this target penetration amplitude is achieved and to adjust the amplitude and/or frequency of vibration to increase the vibration force accordingly, based on Eq. 4:

$$F = A \cdot f^2 \qquad (4).$$

Thus, in such a mode of operation, at the beginning of a penetration cycle, the apparatus may be placed at a first surface of an occlusion, and series of vibration cycles is initiated wherein the control unit controls the force of vibration in response to information from the tissue sensor by adjusting the frequency and/or amplitude of vibration. Once the first surface is penetrated, the apparatus may be advanced to a new face or surface of the occlusion, and a new penetration cycle may be commenced. In this way, the surface of the occlusion may be penetrated in a step-by-step fashion.

Preferably, a penetration cycle (P) begins after initializing the control unit with control information—values relating to amplitude, frequency and vibration adjustment iterations. The control information may be built into the control unit or may be set by the operator. In the embodiment depicted in FIG. 10, the control unit receives the control information from the operator, who sets the initial (target) displacement or amplitude ($A_0$), a maximal displacement ($A_{max}$)—taking into account safety considerations, an initial frequency ($f_0$)—based on assessment of the plaque density, a maximal frequency ($f_{max}$), and a maximal iteration ($I_{max}$). The target amplitude may be, for example, between about 20 μm and about 200 μm. The maximum amplitude may be determined by the operator, for example, based on the lumen diameter and other factors familiar to the skilled artisan. The initial frequency and maximum frequency may be determined by the operator based on, for example, the particular occlusion to be penetrated and the physical limits of the apparatus or system being used. The control unit preferably has an iteration counter for counting iterations in which the vibration force is changed. The iteration count is not a measure of the number of vibration cycles, rather the iteration count is increased only when frequency and/or amplitude are increased. Thus, a vibration cycle may or may not include an adjustment of frequency and/or amplitude, depending on the achieved amplitude (see below). A maximum iteration value may provide either a safety measure (as it may reflect increase in vibration force, as shown below) or a means for an operator to periodically assess the success of the penetration cycle and make adjustments to the procedure as necessary, or both. The series of vibration cycles in the penetration cycle preferably are continuous until the penetration cycle is stopped either by the control unit or the operator. Thus, as used herein, "beginning" or "initiating" a vibration cycle is meant the point in the series of vibrations after the achieved amplitude is compared to the control information. A vibration cycle may be based on units of time or the number of vibrations. Specifically, a vibration cycle can be a predetermined length of time (e.g., 5 seconds or 10 seconds) or a predetermined number of vibration peaks (frequency×time, e.g., number of times the occlusion impact element contacts the occlusion face).

In accordance with the control scheme embodiment illustrated in FIG. 10, after receiving the control information, the control unit sets the iteration count at zero (Step 1). The vibrational energy source is made to generate hydraulic energy pulses into the hydraulic lumen of the hydraulic catheter, and a vibration cycle (V) is begun (Step 2). Distal displacement, or achieved amplitude (A), is measured, preferably via the tissue sensor, and periodically transmitted to be received by the control unit (Step 3), which compares the achieved amplitude (A) to the target amplitude ($A_O$) (Step 4). If the achieved amplitude is less than target amplitude, then an iteration count is added (Step 5a), i.e., I+1, and the working amplitude ($A_i$) and/or working frequency ($f_i$) increased (Step 6) to increase vibration force, in accordance with Eq. 5:

$$F = A_i \cdot f_i^2 \qquad (5),$$

where subscript "i" reflects the current iteration count. The force of the oscillated system is proportional to the square of the frequency and amplitude, as shown in Eq. 4 and 5. It is believed that, from a clinical perspective it is better to work at low amplitude, preferably in the range of up to approximately 100 μm (0.1 mm). Thus, to maintain safety of the occlusion penetration procedure, is preferable to increase force by increasing frequency, however the physical structure of the apparatus may impose upper limits on the frequency. So to achieve adequate force for penetration of an occlusion, either frequency or amplitude may be increased up to the maximum values set in the control information. The gain of the amplitude and/or frequency may be increased by about 2% to about 5% each iteration. Thus, for a given total increase in force in a penetration cycle, the number of iteration counts may depend on the percent gain used.

After the vibration force is increased, the iteration count (I) is compared to the maximum iteration value ($I_{max}$), and the working amplitude ($A_i$) and working frequency ($f_i$) are compared to maximum amplitude ($A_{max}$) and maximum frequency ($f_{max}$), respectively (Step 7). If the iteration count is less than the maximum iteration value, or if the working amplitude is less than the maximum amplitude and the working frequency is less than the maximum frequency, the next vibration cycle is initiated (Step 2) at the new working amplitude, new working frequency and new iteration count; the achieved amplitude (A) is again received (Step 3) and compared to the initial (target) displacement ($A_O$) (Step 4), and the cycle continues. However, if after increasing the force, the iteration count is not less than the maximum iteration value, and the working amplitude is not less than the maximum amplitude or the working frequency is not less than the maximum frequency, then the vibration cycle and penetration cycle are stopped (Step 8), and the apparatus may be repositioned within the lumen and a new penetration cycle commenced, or the occlusion penetration is ended.

If, after comparing the measured displacement (achieved amplitude, A) to target amplitude ($A_O$) (Step 4), the achieved amplitude is not less than the target amplitude, then the achieved amplitude (A) is compared to the maximum amplitude ($A_{max}$) (Step 5b). If the achieved amplitude is less than the maximum amplitude, the iteration count set to zero (Step 1), and a new vibration cycle is initiated (Step 2) at the same working frequency and working amplitude, etc. However, if the achieved amplitude is not less than the target amplitude (Step 4) and also is not less than the maximum amplitude (Step 5b), the vibration cycle and penetration cycle are stopped (Step 8), and the apparatus may be repositioned within the lumen and a new penetration cycle commenced, or the occlusion penetration is ended.

Thus, a method of controlling the frequency and amplitude vibration, and hence the force of vibration, of the apparatus of the invention is provided. In one embodiment, the method for controlling a force of vibration is based on the scheme depicted in FIG. 10. Thus, one method of controlling a force of vibration comprises: a) receiving initial control parameters; b) initiating a vibration iteration cycle comprising at least one hydraulic pressure wave sufficient to vibrate a vibratable member at a vibration force (F); c) receiving an achieved amplitude value input for said vibration iteration cycle; and d) adjusting said vibration force in accordance with said achieved amplitude value. The step of receiving control information may further include: (i) receiving a target amplitude value input; ii) receiving a maximum amplitude value input; iii) receiving an initial frequency value input; iv) receiving a maximum frequency value input; and v) receiving a maximum iteration value input. The step of initiating a vibration cycle may further include: (i) initializing an iteration count to zero; and (ii) commencing said vibration iteration cycle in said apparatus, wherein said at least one hydraulic pressure wave occurs at an initial frequency and a target amplitude. The step of adjusting said vibration force may further include: (i) comparing said achieved amplitude value to a target amplitude value and to a maximum amplitude value; (ii) increasing said iteration count by one when said achieved amplitude value is less than said target amplitude value, setting said iteration count to zero when said achieved amplitude value is not less than said target amplitude value, and stopping said vibration iteration cycle when said achieved amplitude value is not less than said target amplitude value and not less than said maximum amplitude value; and (iii) increasing said force of vibration by increasing a frequency gain and/or an amplitude gain by 2-5% in accordance with the equation $F=A_i \times f_i^2$ to generate a new working frequency ($f_i$) and/or a new working amplitude ($A_i$) if said iteration count is increased by one. This embodiment of the method of controlling a force of vibration may further comprise: e) comparing said iteration count to a maximum iteration value, comparing said working amplitude to a maximum amplitude value, and comparing said working frequency to a maximum frequency value; f) initiating a new vibration iteration cycle in said apparatus: if said iteration count is less than said iteration maximum value, or if said working amplitude is less than said maximum amplitude value and said working frequency is less than said maximum frequency value; and g) stopping said vibration iteration cycle: if said iteration count is not less than said iteration maximum value, and if said working amplitude is not less than said maximum amplitude value or said working frequency is not less than said maximum frequency value.

In another aspect of this embodiment the method comprises: a) receiving a target amplitude value input, a maximum amplitude value input, a target frequency value input, a maximum frequency value input, and a maximum iteration count input; b) initializing an iteration count to zero; c) initiating a vibration iteration cycle comprising at least one hydraulic pressure wave sufficient to vibrate said vibratable member for an iteration at a force of vibration (F); d) receiving an achieved amplitude value input for said vibration iteration cycle; e) comparing said achieved amplitude value to said target amplitude value; f) increasing said iteration count by one and increasing said force of vibration by increasing a frequency gain and/or an amplitude gain by 2-5% in accordance with the equation $F=A_i \times f_i^2$ to generate a working frequency ($f_i$) and/or an working amplitude ($A_i$) if said achieved amplitude value is less than said target amplitude value, and then proceeding to step k); g) comparing said achieved amplitude value to said maximum amplitude value if said achieved amplitude value is not less than said target amplitude value; h) initializing said iteration count to zero if said achieved amplitude value is less than said maximum amplitude value, and recommencing method at step (c); i) proceeding to step (m) if said achieved amplitude value is not less than said maximum amplitude value; j) comparing said iteration count to said maximum iteration count, comparing said working amplitude to said maximum amplitude value and comparing said working frequency to said maximum frequency value; k) recommencing method at step (c): if said iteration count is less than said maximum iteration count, or if said working amplitude is less than said maximum amplitude value and said working frequency is less than said maximum frequency value; l) proceeding to step (m): if said iteration count is not less than said maximum iteration count, and if either said working amplitude is not less than said maximum amplitude value or said working frequency is not less than said maximum frequency value; and m) stopping said vibration iteration cycle.

The above-described embodiment is only exemplary and is not intended to limit the ways in which a control unit might operate. Any number of control schemes for adjusting the frequency and/or amplitude of the hydraulic pressure wave (and thus the frequency and amplitude of vibration) may be used. Other methods for control unit operation should be within the skill in the art in view of the disclosure herein. For example, a control scheme may include reducing the vibration force by decreasing the working amplitude when the achieved amplitude is not less than the target amplitude and not less than the maximum amplitude for one or more iterations, before stopping the vibration cycle and penetration cycle.

As described above, there are several ways to monitor the achieved amplitude (A). It can be done directly using a strain gauge or indirectly by measuring pressure in the hydraulic system, or by measuring the displacement of either or both the proximal or distal bellows. Preferably, the occlusion penetration procedure begins at a minimal force, which is gradually increased according to the hardness of the tissue. A control algorithm also may be used to calculate the force required based on the feedback regarding occlusion hardness.

The invention also relates to a method of treating an occlusion in a body lumen using any of the above-described apparatuses or systems. The method generally comprises: a) introducing into a body lumen having an occlusion a hydraulic catheter having a distal end and a catheter head at said distal end, wherein said hydraulic catheter is operably connected to a vibrational energy source; (b) advancing said hydraulic catheter until said catheter head contacts a first face of said occlusion; (c) generating a plurality of hydraulic pressure waves via said vibrational energy source into said hydraulic catheter sufficient to vibrate a vibratable member, wherein said vibratable member is located in said catheter head and said plurality of hydraulic pressure waves comprises at least one frequency and at least one amplitude; and (d) using said vibrations of said vibratable member to penetrate said first face of said occlusion. The method may further comprise the steps of e) stopping said vibration; (f) advancing said hydraulic catheter to contact a new face of said occlusion; (g) repeating steps (a)-(d) until said new face of said occlusion is penetrated; and (h) repeating steps (a)-(g) until said occlusion is completely penetrated. The method may alternatively comprise the step of (e) repeating steps (a)-(d) until said first face of said occlusion is penetrated. This method may then further include (f) stopping said vibration; (g) advancing said hydraulic catheter to contact a new face of said occlusion; (h) repeating steps (a)-(d) until said new face of said occlusion is penetrated; and (i) repeating steps (a)-(h) until said occlusion is completely penetrated. The method may further include the step of adjusting said at least one frequency and/or said at least one amplitude of vibration via a control unit based on occlusion hardness. Preferably, where the vibration frequency is adjusted to achieve an appropriate force based on information regarding occlusion hardness, said hydraulic catheter includes a tissue sensor and said occlusion hardness is determined from information from said tissue sensor. In some embodiments, the adjusting step may be performed manually, in other embodiments the adjusting step may be performed automatically. In particular, the method may comprise treating a chronic total occlusion in a blood vessel.

As is evident by the descriptions above, the apparatus and system are compatible for use with guide wires, which are useful for guiding a catheter through a body lumen, in particular for guiding a catheter through a blood vessel. Stiff guide wires are used in the art for recanalizing blood vessel occlusion. In some cases, physicians prefer to use a stiff guide wire to penetrate a vascular occlusion but demand additional means to effect penetration where the occlusion is particularly difficult and perhaps safety is a concern. The apparatus and system of the invention provide that additional means; the apparatus and system of the invention are compatible with using a stiff guide wire in addition to the hydraulic system to penetrate blood vessel occlusions, including total chronic occlusions. Accordingly, the invention encompasses a method of treating a chronic total occlusion in a body lumen (where the vibratable member of the hydraulic catheter is not a guide wire) by supplementing the method of penetrating an occlusion described above with using the tip of a guide wire to penetrate the occlusion. In particular, in this embodiment said hydraulic catheter includes a stiff guide wire, and said method further comprises advancing said stiff guide wire to penetrate said face of said occlusion alternately with (c) generating a plurality of hydraulic pressure waves via said vibrational energy source into said hydraulic catheter sufficient to vibrate a vibratable member, wherein said plurality of hydraulic pressure waves comprises at least one frequency and at least one amplitude, and said vibratable member is located in said catheter head; and (d) using said vibrations of said vibratable member to penetrate said first face of said occlusion.

As the apparatus and system are compatible for use with imaging components, the apparatus or system of the invention may further comprise imaging components and an imaging system, for example, IVUS, OCR, Doppler ultrasound or other imaging systems known in the art.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. An apparatus, comprising: a hydraulic catheter; and a vibrational energy source operably connected to said hydraulic catheter, wherein said hydraulic catheter includes a hydraulic tube extending from a proximal end to a distal end and having a proximal bellows at said proximal end and a distal bellows at said distal end, wherein said vibrational energy source is adapted to generate at least one hydraulic pressure wave into said hydraulic tube, the hydraulic pressure wave propagated by said proximal bellows to energize said distal bellows to generate an oscillation of said distal bellows, wherein said at least one hydraulic pressure wave has at least one frequency and at least one amplitude, wherein said hydraulic tube is capable of transmitting said at least one hydraulic pressure wave to said distal bellows.

2. The apparatus according to claim 1, wherein said hydraulic catheter further includes a guide wire lumen and a guide wire.

3. The apparatus of claim 2, wherein said distal bellows comprises a spring, an extensible housing and an extensible interior lumen wall.

4. The apparatus according to claim 2 or 3, wherein said guide wire lumen includes one or more extensible sections.

5. The apparatus according to claim 1, wherein said hydraulic catheter has a distal end and includes at said distal end a catheter head comprising a member vibratable by hydraulic pressure waves, and a second hydraulic tube having a second proximal bellows, a second distal bellows, wherein said second hydraulic tube sealingly connects said second proximal bellows to said second distal bellows.

6. The apparatus according to claim 5, wherein said first distal bellows is a first expandable membrane, and said second distal bellows is a second expandable membrane.

7. The apparatus according to claim 6, wherein said vibrational energy source is adapted to generate a plurality of first hydraulic pressure waves into said first hydraulic tube to expand said first expandable membrane and a plurality of second hydraulic pressure waves into said second hydraulic tube to expand said second expandable membrane, and wherein said vibratable member is capable of being oscillated by alternating expansion of said first expandable membrane and said second expandable membrane.

8. The apparatus according to claim 7, wherein said vibratable member is the distal end of a guide wire capable of oscillating by being reversibly flexed, said distal end having an impact end at its distal tip, and wherein said hydraulic catheter further includes at least one guide wire anchoring device.

9. The apparatus according to claim 1 or 8, further comprising a hydraulic catheter anchoring device.

10. The apparatus according to claim 9, wherein said hydraulic catheter anchoring device is an expandable balloon.

11. The apparatus according to claim 1 or 8, further comprising a catheter head steering device.

12. The apparatus according to claim 1, wherein the hydraulic tube is fluidly sealed at the distal end.

13. The apparatus according to claim 1, wherein the proximal bellows has a resting configuration and a contracted configuration.

14. A system, comprising:
  a. a hydraulic catheter comprising a hydraulic tube having a proximal bellows at a proximal end, a distal bellows at a distal end, wherein the hydraulic tube is fluidly sealed at the distal end;
  b. a vibrational energy source operably connected to said hydraulic catheter; and
  c. a control unit adapted to control said vibrational energy source;
    wherein said vibrational energy source is adapted to generate at least one hydraulic pressure wave into said hydraulic tube via said proximal bellows, wherein said at least one hydraulic pressure wave has at least one frequency and at least one amplitude, wherein said hydraulic tube is capable of transmitting said at least one hydraulic pressure wave to said distal bellows, and wherein said distal bellows is capable of being energized by said at least one hydraulic pressure wave to generate a vibration.

15. The system according to claim 14, wherein said at least one frequency and/or said at least one amplitude are independently adjustable via said control unit.

16. The system according to claim 14, wherein said control unit includes an adjustor means for manually adjusting said at least one frequency and said at least one amplitude.

17. The system according to claim 14, wherein said control unit is operably connected to a processor, and wherein said hydraulic catheter further includes a tissue sensor adapted to measure occlusion hardness and transmit information regarding said occlusion hardness to said processor.

18. The system according to claim 17, wherein said control unit is capable of adjusting said at least one frequency and/or said at least one amplitude automatically.

19. The system according to claim 17, wherein said control unit and processor are operably connected to an operator interface unit.

20. The system according to claim 19, wherein said operator interface unit includes a display unit capable of displaying said occlusion hardness information as operator-readable output.

21. The system according to claim 20, wherein said control unit or operator interface unit includes an adjustor means for manually adjusting said at least one frequency and/or said at least one amplitude.

22. The system according to claim 17, wherein said information transmitted to said processor includes an achieved amplitude of vibration, wherein said control unit and/or processor are adapted to receive a target amplitude value input, a maximum amplitude value input, an initial frequency input, a maximum frequency value input, and a maximum iteration value input, wherein said control unit is adapted to count iterations, adjust amplitude gain, and adjust frequency gain, and wherein said control unit is adapted to control said vibrational energy source by adjusting said at least one frequency and/or said at least one amplitude according to a value of said achieved amplitude of vibration.

23. The system according to claim 14, wherein said hydraulic catheter has a distal end and includes at said distal end a vibratable member, a second hydraulic tube having a second proximal bellows, a second distal bellows, said second hydraulic tube sealingly connecting said second proximal bellows to said second distal bellows.

24. The system according to claim 23, wherein said first distal bellows is a first expandable membrane, and said second distal bellows is a second expandable membrane.

25. The system according to claim 24, wherein said vibrational energy source is adapted to generate (i) a plurality of first hydraulic pressure waves into said first hydraulic tube via said first proximal bellows to expand said first expandable bellows, and (ii) a plurality of second hydraulic pressure waves into said second hydraulic tube via said second proximal bellows to expand said second expandable bellows, and wherein said vibratable member is capable of being oscillated by alternating expansion of said first expandable membrane and said second expandable membrane.

26. The system according to claim 25, wherein said vibratable member is a distal end of a guide wire capable of oscillating by being reversibly flexed, said distal end having an impact end at its distal tip, and wherein said hydraulic catheter further includes at least one guide wire anchoring device.

27. The system according to claim 26, wherein said plurality of first hydraulic pressure waves have a first at least one frequency and a first at least one amplitude, and said plurality of second hydraulic pressure waves have a second at least one frequency and a second at least one amplitude.

28. The system according to claim 27, wherein said first and second at least one frequency and said first and second at least one amplitude are independently adjustable via said control unit.

29. The system according to claim 28, wherein said control unit comprises one or more adjustor means for manually adjusting said first and second at least one frequency and/or said first and second at least one amplitude.

30. The system according to claim 28, wherein said control unit is operably connected to a processor, and wherein said hydraulic catheter further includes a tissue sensor adapted to measure occlusion hardness and transmit information regarding said occlusion hardness to said processor.

31. The system according to claim 30, wherein said control unit is capable of adjusting said at least one frequency and said at least one amplitude automatically.

32. The system according to claim 30, wherein said control unit and processor are operably connected to an operator interface unit.

33. The system according to claim 32, wherein said operator interface unit includes a display unit capable of displaying said occlusion hardness information as operator-readable output.

34. The system according to claim 15 or 28, further comprising an imaging system, and wherein said hydraulic catheter further includes a visualization or imaging component lumen.

35. The system according to claim 15 or 28, wherein said hydraulic catheter further includes a catheter anchoring device.

36. The system according to claim 35, wherein said catheter anchoring device is an expandable balloon.

37. The system according to claim 15 or 28, further comprising a catheter head steering device.

38. A method of oscillating the guide wire of the system of claim 26, comprising:
 (a) locking said distal end of said guide wire relative to a remainder of said guide wire by engaging said at least one guide wire anchoring device;
 (b) generating a plurality of first hydraulic pressure waves from said vibrational energy source into said first hydraulic tube and a plurality of second hydraulic pressure waves from said vibrational energy source into said second hydraulic tube, wherein said plurality of first hydraulic pressure waves are 180 degrees out of phase with said plurality of second hydraulic pressure waves.

39. The system according to claim 14, wherein the proximal bellows has a resting configuration and a contracted configuration.

40. An apparatus, comprising:
 a hydraulic catheter; and a vibrational energy source operably connected to said hydraulic catheter, wherein said hydraulic catheter includes a hydraulic tube extending from a proximal end having a proximal element to a distal end having distal element;

wherein the proximal element is one of a bellows and an elastic membrane movable between a resting configuration and a contracted configuration wherein the distal element is selected from the group consisting of a bellows, elastic membrane, a driving surface of a vibration cap, a distal impact end of a guide wire and a spring embedded in an extensible housing.

41. The apparatus according to claim 40, wherein said hydraulic catheter further includes a guide wire lumen and a guide wire.

42. The apparatus of claim 41, wherein said distal element comprises a spring embedded in an extensible housing, the distal element further comprising an extensible interior lumen wall.

43. The apparatus according to claim 42, wherein said guide wire lumen includes one or more extensible sections.

44. The apparatus according to claim 40, further comprising a second hydraulic tube having a second proximal element, a second distal element, wherein said second hydraulic tube sealingly connects said second proximal element to said second distal element.

45. The apparatus according to claim 40, further comprising a hydraulic catheter anchoring device.

46. The apparatus according to claim 45, wherein said hydraulic catheter anchoring device is an expandable balloon.

47. The apparatus according to claim 40, further comprising a catheter head steering device.

48. The apparatus according to claim 40, wherein the hydraulic tube is fluidly sealed at the distal end.

49. The apparatus according to claim 40, wherein the proximal bellows has a resting configuration and a contracted configuration.

* * * * *